US010695757B2

(12) United States Patent
Brunelli et al.

(10) Patent No.: US 10,695,757 B2
(45) Date of Patent: Jun. 30, 2020

(54) ZEOLITIC MATERIALS INCLUDING PAIRED LEWIS ACID CATALYTIC SITES

(71) Applicant: Ohio State Innovation Foundation, Columbus, OH (US)

(72) Inventors: Nicholas Brunelli, Columbus, OH (US); Nitish Deshpande, Columbus, OH (US); Aamena Parulkar, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 401 days.

(21) Appl. No.: 15/815,413

(22) Filed: Nov. 16, 2017

(65) Prior Publication Data

US 2018/0133700 A1    May 17, 2018

Related U.S. Application Data

(60) Provisional application No. 62/422,962, filed on Nov. 16, 2016.

(51) Int. Cl.
*C01B 39/06* (2006.01)
*C01B 39/08* (2006.01)
(Continued)

(52) U.S. Cl.
CPC ........... *B01J 29/7057* (2013.01); *B01J 29/40* (2013.01); *B01J 29/405* (2013.01); *B01J 29/48* (2013.01); *B01J 29/70* (2013.01); *B01J 29/7007* (2013.01); *B01J 29/7815* (2013.01); *B01J 35/1019* (2013.01); *B01J 35/1038* (2013.01);
(Continued)

(58) Field of Classification Search
CPC . B01J 29/40; B01J 29/405; B01J 29/48; B01J 29/70; B01J 29/7007; B01J 29/7057; B01J 29/7815; C01B 39/06; C01B 39/08; C01B 39/082; C01B 39/085; C01B 39/38; C01B 39/40; C01B 39/48; C07H 1/00; C07H 3/02
See application file for complete search history.

(56) References Cited

U.S. PATENT DOCUMENTS 5,110,576 A * 5/1992 Soeda ............... C08K 3/04
423/445 R
5,399,336 A * 3/1995 Guth ............... B01J 29/04
423/326

(Continued)

OTHER PUBLICATIONS

Adleman et al. Heterogenous Catalysis Mediated by Plasmon Heating. Nano Lett 2009; 9(12), 4417-4423.

(Continued)

*Primary Examiner* — David M Brunsman
(74) *Attorney, Agent, or Firm* — Meunier Carlin & Curfman LLC

(57) ABSTRACT

Disclosed are zeolitic materials that include a microporous crystalline framework substituted with one or more paired Lewis acid sites. Each of the one or more paired Lewis acid sites within the zeolitic material can comprise a first Lewis acid metal center and a second Lewis acid metal center. The first Lewis acid metal center and the second Lewis acid metal center can be separated by three or fewer atoms within the crystalline framework. Also provided herein are methods of making these zeolitic materials as well as methods of using these zeolitic materials as catalysts.

20 Claims, 16 Drawing Sheets

(51) Int. Cl.
| | |
|---|---|
| C01B 39/38 | (2006.01) |
| C01B 39/40 | (2006.01) |
| C01B 39/48 | (2006.01) |
| B01J 29/40 | (2006.01) |
| B01J 29/48 | (2006.01) |
| B01J 29/70 | (2006.01) |
| C01B 39/46 | (2006.01) |
| C07H 3/02 | (2006.01) |
| B01J 37/04 | (2006.01) |
| B01J 37/03 | (2006.01) |
| C07H 1/00 | (2006.01) |
| C01B 37/00 | (2006.01) |
| B01J 35/10 | (2006.01) |
| B01J 29/78 | (2006.01) |

(52) U.S. Cl.
CPC ............. *B01J 37/036* (2013.01); *B01J 37/04* (2013.01); *C01B 37/002* (2013.01); *C01B 39/06* (2013.01); *C01B 39/08* (2013.01); *C01B 39/085* (2013.01); *C01B 39/38* (2013.01); *C01B 39/40* (2013.01); *C01B 39/46* (2013.01); *C01B 39/48* (2013.01); *C07H 1/00* (2013.01); *C07H 3/02* (2013.01)

(56) References Cited

U.S. PATENT DOCUMENTS

| | | | | |
|---|---|---|---|---|
| 5,968,473 | A * | 10/1999 | Valencia | C01B 39/085 423/326 |
| 6,306,364 | B1 * | 10/2001 | Valencia | C01B 39/085 423/326 |
| 9,108,190 | B1 * | 8/2015 | Fan | B01J 29/89 |

OTHER PUBLICATIONS

Bermejo-Deval et al. Active Sites in Sn-Beta for Glucose Isomerization to Fructose and Epimerization to Mannose. ACS Catal. 2014, 4, 2288-2297.
Boronat et al. Determination of the catalytically active oxidation Lewis acid sites in Sn-beta zeolites, and their optimization by the combination of theoretical and experimental studies. J. Catal. 2005, 234, 111-118.
Camblor et al. Characterization of nanocrystalline zeolite Beta. Micro Meso Mat 1998, 25 (1-3), 59-74.
Camblor et al. Spontaneous nucleation and growth of pure silica zeolite-β free of connectivity defects. Chem. Commun. 1996, (20), 2365-2366.
Christopher et al. Enhancing photochemical activity of semiconductor nanoparticles with optically active Ag nanostructures: photochemistry mediated by Ag surface plasmons. J. Phys. Chem. C 2010, 114 (19), 9173-9177.
Christopher et al. Visible-light-enhanced catalytic oxidation reactions on plasmonic silver nanostructures. Nature Chemistry 2011, 3 (6), 467-472.
Corma et al. Al-free Sn-Beta zeolite as a catalyst for the selective reduction of carbonyl compounds (Meerwein-Ponndorf-Verley reaction). J. Am. Chem. Soc. 2002, 124, 1-3.
Corma et al. Sn-zeolite beta as a heterogeneous chemoselective catalyst for Baeyer-Villiger oxidations. Nature. 2001, 412, 423-425.
Davies et al. Asymmetric cyclopropanations by rhodium (II) N-(arylsulfonyl) prolinate catalyzed decomposition of vinyldiazomethanes in the presence of alkenes. Practical nantioselective synthesis of the four stereoisomers of 2-phenylcyclopropan-1-amino acid. J. Am. Chem. Soc. 1996, 118, 6897-6907.
Eustis et al. Why gold nanoparticles are more precious than pretty gold: Noble metal surface plasmon resonance and its enhancement of the radiative and nonradiative properties of nanocrystals of different shapes. Chem. Soc. Rev. 2006, 35 (3), 209.
Harris et al. Titration and quantification of open and closed Lewis acid sites in Sn-Beta zeolites that catalyze glucose isomerization. J. Catal. 2016, 335, 141-154.
Ikeda et al. Photoinduced dynamics of TiO2 doped with Cr and Sb. J. Phys. Chem. C 2008, 112 (4), 1167-1173.
Ikeda et al. Time-resolved infrared spectroscopy of K3Ta3B2O12 photocatalysts for water splitting. The Journal of Physical Chemistry B 2006, 110 (15), 7883-7886.
Ikonomou et al. Electrospray mass spectrometry of methanol and water solutions suppression of electric discharge with SF6 gas. Journal of the American Society for Mass Spectrometry 1991, 2 (6), 497-505.
Jones et al. Organic-functionalized molecular sieves as shape selective catalysts. Nature. 1998, 393, 52-54.
Kebarle et al. Electrospray: From ions in solution to ions in the gas phase, what we know now. Mass Spectrom. Rev. 2009, 28 (6), 898-917.
Konsler et al. Cooperative asymmetric catalysis with dimeric salen complexes. J. Am. Chem. Soc. 1998, 120, 10780-10781.
Kovalevsky et al. Metal Ion Roles and the Movement of Hydrogen during Reaction Catalyzed by D-Xylose Isomerase : A Joint X-Ray and Neutron Diffraction Study. Structure. 2010, 18, 688-699.
Lewis et al. Acid-Base Pairs in Lewis Acidic Seolites Promote Direct Aldol Reactions by Soft Enolization. Angew. Chem. Int. Ed. 2015, 54(34), 9835-9838.
Loo et al. Immunotargeted nanoshells for integrated cancer imaging and therapy. Nano Lett 2005, 5(4), 709-711.
Maeda et al. GaN:ZnO solid solution as a photocatalyst for visible-light-driven overall water splitting. J Am Chem Soc 2005, 127 (23), 8286-8287.
Maeda et al. Photocatalyst releasing hydrogen from water. Nature 2006, 440(7082), 295-295.
Moliner et al. Tin-containing zeolites are highly active catalysts for the isomerization of glucose in water. Proc. Nat. Acad. Sci. 2010, 107, 6164-6168.
Osterloh, Inorganic materials as catalysts for photochemical splitting of water. Chem. Mater 2007, 20 (1), 35-54.
Raders et al. Catalysis of mukaiyama aldol reactions by a tricyclic aluminum alkoxide Lewis acid. J. Org. Chem. 2009, 74, 5417-28.
Snell et al. Optimizing crystal volume for neutron diffraction: D-xylose isomerase. Eur. Biophys. J. 2006, 35, 621-632.
Takewaki et al. Synthesis of CIT-6 , a zincosilicate with the ?BEA topology. Top. Catal 1999, 9, 35-42.
Tang et al. Improved Post-synthesis strategy to Sn-Beta zeolites as Lewis acid catalysts for the ring-open hydration of epoxides. ACS Catalysis, 2014, 4(8), 2801-2810.
Taylor, Disintegration of water drops in an electric field. Proceedings of the Royal Society of London. Series A 1964, 280, 383-397.
Van De Vyver et al. Solid Lewis Acids Catalyze the Carbon-Carbon Coupling between Carbohydrates and Formaldehyde. ACS Catal. 2015, 5, 972-977.
Wampler et al. Negative ion electrospray mass spectrometry of nucleotides: ionization from water solution with SF6 discharge suppression. Journal of the American Society for Mass Spectrometry 1993, 4 (4), 289-295.
Wolf et al. Post-synthetic preparation of Sn-, Ti- and Zr-beta: a facile route to water tolerant, highly active Lewis acidic zeolites. Dalton Trans. 2014, 43, 4514-9.
Xie et al. Synthesis of bifunctional Au/Pt/Au core/shell nano-raspberries for in-situ SERS monitoring of platinum-catalyzed reactions. J Am Chem Soc. 2011, 133(48), 19302-19305.
Yamakata et al. Time-resolved infrared absorption spectroscopy of photogenerated electrons in platinized TiO2 particles. Chemical physics letters 2001, 333 (3-4), 271-277.
Yamakata et al. Time-Resolved Infrared Absorption Studies of Surface OH Groups on TiO 2 Particles Irradiated by UV Pulses. Bulletin of the Chemical Society of Japan 2002, 75 (5), 1019-1022.
Yamakata et al. Time-resolved infrared absorption study of nine TiO2 photocatalysts. Chemical Physics 2007, 339 (1-3), 133-137.
Yamamoto et al. Organic-inorganic hybrid zeolites containing organic frameworks. Science. 2003, 300, 470-2.
Yamamoto et al. ZOL : A New Type of Organic—Inorganic Hybrid Zeolites. Chem. Mater. 2008, 20, 972-980.

(56) References Cited

OTHER PUBLICATIONS

Yang et al. Structure, Stability, and Lewis Acidity of Mono and Double Ti, Zr, and Sn Framework Substitutions in BEA Zeolites: A Periodic Density Functional Theory Study. J. Phys. Chem. C. 2013, 117, 3976-3986.

Zielasek et al. Gold Catalysts: Nanoporous Gold Foams. Angew. Chem. Int. Ed. 2006, 45 (48), 8241-8244.

Zobel et al. α, ω-Bis (trichlorostannyl) alkanes: unravelling the hydrolysis pathway to organotin-oxo oligomers. Organometallics. 2001, 20, 2820-2826.

\* cited by examiner

ZEOLITIC MATERIALS INCLUDING PAIRED LEWIS ACID CATALYTIC SITES

CROSS REFERENCE TO RELATED APPLICATIONS

This application claims benefit of U.S. Provisional Patent Application No. 62/422,962, filed Nov. 16, 2016, which is hereby incorporated herein by reference in its entirety.

BACKGROUND

Zeolites are widely used as solid acid catalysts for conversion of biomass and petroleum-based feedstocks to chemicals and fuels. While the predominant use of zeolites remains for Brønsted acid catalyzed reactions, the catalytic capabilities of zeolites have greatly expanded with the introduction of Lewis acidic zeolites, such as TS-1, CIT-6, Sn-BEA, and other Lewis acidic zeolites. These powerful Lewis acidic zeolites can catalyze a whole new landscape of intriguing chemical reactions such as Meerwein-Poondorf-Verley reductions (MPV), aldol condensations, and the isomerization of glucose to fructose. Existing Lewis acidic zeolites include isolated metal centers, such as Ti, Zn, Hf, Zr, and Sn. Intriguingly, enzymes that catalyze similar reactions often include pairs of metal centers as opposed to isolated metal centers. In these enzymes, the catalytic pairs of metal centers are thought to increase both selectivity and activity. However, paired metal centers are challenging to achieve in heterogeneous catalytic materials.

Translating these beneficial features of enzymes to heterogeneous catalytic materials has been a longstanding challenge for the field of catalysis. Creating catalysts that include paired sites has been a challenge because heterogeneous catalytic materials typically possess catalytic sites that are non-uniform and/or randomly distributed. Yet, enzymes and homogeneous catalysis clearly demonstrate a benefit to creating catalytic material with paired sites. Numerous examples from homogeneous catalyst demonstrate that catalytic pairs can influence activity and selectivity. The key challenge remains how to achieve these catalytic pairs in heterogeneous catalytic materials such as zeolites. Zeolites are attractive targets since they are crystalline, can be shape selective, and can be made hydrophobic to enable Lewis acid chemistry in water. However, zeolites are highly challenging because these materials are synthesized using crystallization procedures that are only beginning to be understood beyond a phenomenological level.

SUMMARY

Provided herein are zeolitic materials that include a microporous crystalline framework substituted with one or more paired Lewis acid sites. Each of the one or more paired Lewis acid sites within the zeolitic material can comprise a first Lewis acid metal center and a second Lewis acid metal center. The first Lewis acid metal center and the second Lewis acid metal center can be separated by three or fewer atoms within the crystalline framework. For example, the first Lewis acid metal center and the second Lewis acid metal center can be separated by three atoms within the crystalline framework, or separated by one atom within the crystalline framework.

The first Lewis acid metal center and the second Lewis acid metal center can be separated by less than 10 Angstroms (e.g., less than 5 Angstroms, or less than 4 Angstroms), measured metal center to metal center. In certain embodiments, the first Lewis acid metal center and the second Lewis acid metal center are separated by from 2 to 4 Angstroms. In one embodiment, the first Lewis acid metal center and the second Lewis acid metal center are separated by from 2.5 to 3 Angstroms.

In some embodiments, each of the one or more paired Lewis acid sites in the zeolitic material can be defined by the formula below

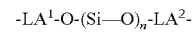
-LA$^1$-O-(Si—O)$_n$-LA$^2$- wherein LA$^1$ represents the first Lewis acid metal center; LA$^2$ represents the second Lewis acid metal center; and n is 0 or 1.

In some embodiments, n is 0, and each of the one or more paired Lewis acid sites in the zeolitic material can be defined by the formula below

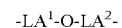
-LA$^1$-O-LA$^2$- wherein LA$^1$ represents the first Lewis acid metal center; and LA$^2$ represents the second Lewis acid metal center. In other embodiments, n is 1, and each of the one or more paired Lewis acid sites in the zeolitic material can be defined by the formula below

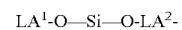
LA$^1$-O—Si—O-LA$^2$- wherein LA$^1$ represents the first Lewis acid metal center and LA$^2$ represents the second Lewis acid metal center.

In some embodiments, the first Lewis acid metal center and the second Lewis acid metal center can independently chosen from Sn, Hf, Zn, Zr, Ti, V, Ta, Ga, Ge, Nb, and Cr. In some embodiments, the first Lewis acid metal center and the second Lewis acid metal center can independently chosen from Sn, Hf, Zr, and Ge.

The first Lewis acid metal center and the second Lewis acid metal center can comprise the same metal or different metals. In some embodiments, the paired Lewis acid site can comprise a homodimer. In these instances, both the first Lewis acid metal center and the second Lewis acid metal center can comprise the same metal. For example, in one embodiment, the first Lewis acid metal center can be Sn and the second Lewis acid metal center can be Sn. In another embodiment, the first Lewis acid metal center can be Zr and the second Lewis acid metal center can be Zr.

In other embodiments, paired Lewis acid site can comprise a heterodimer. In these instances, the first Lewis acid metal center and the second Lewis acid metal center can comprise different metals. For example, in one embodiment, the first Lewis acid metal center can be Sn and the second Lewis acid metal center can be Zr.

The quantity (and by extension concentration) of paired Lewis acid sites included within the microporous crystalline framework of the zeolitic material can be varied. For example, in some embodiments, the molar ratio of paired Lewis acid sites to Si atoms in the zeolitic material can be at least 1:1000 (e.g., at least 1:500, at least 1:400, or at least 1:200). In some embodiments, the molar ratio of paired Lewis acid sites to Si atoms in the zeolitic material can be from 1:1000 to 1:50 (e.g., from 1:400 to 1:50).

The zeolitic material can comprise suitable type of zeolite. For example, the zeolitic material can be of any suitable zeolite structural group (e.g., any suitable Nickel-Strunz classification). In some embodiments, the microporous crystalline framework can comprise BEA. In other embodiments, the microporous crystalline framework can comprise MFI.

Also provided are methods for preparing a zeolitic material that comprise a microporous crystalline framework isomorphously substituted with one or more paired Lewis acid sites. Methods for preparing these zeolitic materials can comprise combining, in aqueous solution, a silicon source, a paired Lewis acid monomer, and optionally a structure-directing agent to form a precursor gel; reacting the precursor gel under conditions effective to form a zeolitic precursor; and treating the zeolitic precursor to form the zeolitic material comprising the microporous crystalline framework isomorphously substituted with one or more paired Lewis acid sites.

In some embodiments, step (i) can comprise combining, in aqueous solution, the silicon source, the paired Lewis acid monomer, and the structure-directing agent to form a precursor gel. In some cases, the structure-directing agent can comprise a quaternary ammonium hydroxide group. For example, the structure-directing agent can comprise a tetraalkyl ammonium hydroxide, such as tetraethyl ammonium hydroxide. The silicon source can comprise, for example, tetraethylorthosilicate.

In some embodiments, the paired Lewis acid monomer can be defined by the formula below

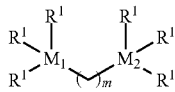

where $M_1$ and $M_2$ are independently chosen from Sn, Hf, Zn, Zr, Ti, V, Ta, Ga, Ge, Nb, and Cr; $R^1$ represents, independently for each occurrence, a halogen; and m is an integer from 1 to 5 (e.g., an integer from 1 to 3).

In some embodiments, m can be 1. In some embodiments, $R^1$ represents Cl.

In some embodiments, $M_1$ and $M_2$ can independently be chosen from Sn, Hf, Zn, Zr, Ti, V, Ta, Ga, Ge, Nb, and Cr. In some embodiments, $M_1$ and $M_2$ can independently be chosen from Sn, Hf, Zr, and Ge.

$M_1$ and $M_2$ can comprise the same metal or different metals. In some embodiments, the paired Lewis acid monomer can comprise a homodimer. In these instances, both $M_1$ and $M_2$ can comprise the same metal. For example, in one embodiment, $M_1$ can be Sn and $M_2$ can be Sn. In another embodiment, $M_1$ can be Zr and $M_2$ can be Zr.

In other embodiments, paired Lewis acid monomer can comprise a heterodimer. In these instances, $M_1$ and $M_2$ can comprise different metals. For example, in one embodiment, $M_1$ can be Sn and $M_2$ can be Zr.

In some embodiments, step (ii) can comprise incubating the precursor gel to hydrolyze the silicon source. This can comprise, for example, incubating the precursor gel for a period of from 12 hours to 72 hours at a temperature of from 20° C. to 40° C. In some embodiments, step (ii) can comprise heating the precursor gel in the presence of zeolite seed crystals to form the zeolitic precursor. Appropriate zeolite seed crystals can be selected in view of the desired morphology for the resulting zeolitic material. For example, in embodiments where the zeolitic material has a microporous crystalline framework that comprises BEA, step (ii) can comprise heating the precursor gel in the presence of BEA seed crystals to form the zeolitic precursor. In some embodiments, step (ii) can comprise heating the precursor gel in the presence of a fluoride source (e.g., $NH_4F$, $NH_4HF_2$, HF, or a combination thereof) to form the zeolitic precursor.

In some embodiments, step (iii) can comprise calcining the zeolitic precursor to form the zeolitic material comprising the microporous crystalline framework isomorphously substituted with one or more paired Lewis acid sites. For example, step (iii) can comprise heating the zeolitic precursor in air at a temperature of from 400° C. to 750° C. (e.g., at a temperature of about 550° C.). In some embodiments, step (iii) can comprise extracting the zeolitic precursor (e.g., by flowing an appropriate solvent through the zeolitic precursor) to form the zeolitic material comprising the microporous crystalline framework isomorphously substituted with one or more paired Lewis acid sites.

Zeolitic materials that include paired Lewis acid sites can exhibit improved catalytic activity (e.g., improved selectivity) relative to zeolites that include isolated Lewis acid sites. Accordingly, the zeolitic materials described herein can be used at heterogeneous catalysts in a wide variety of reactions that employ Lewis acid catalysts. For example, the zeolitic materials described herein can be used to catalyze the isomerization of sugars (e.g., the isomerization of glucose to fructose), Meerwein-Poondorf-Verley reductions (MPV), aldol condensations, Diels-Alder reactions, dehydrogenation reactions (e.g., the dehydrogenation of propane to propylene), and the synthesis of dimethylcarbonate from carbon dioxide.

DESCRIPTION OF DRAWINGS

As shown in FIG. 16C, at similar levels of percent conversion, PC100 exhibited a higher fructose/Mannose ratio.

DETAILED DESCRIPTION

Figure 1A:
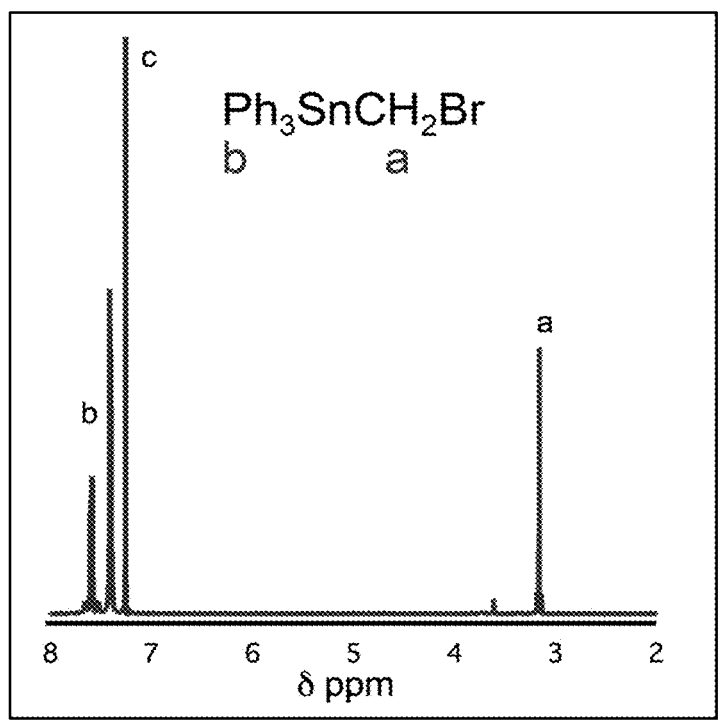
FIG. 1A shows the $^1H$ NMR spectra of (bromomethyl)triphenylstannane (3) in $CDCl_3$: δ 3.16 ppm (s, 2H, $CH_2$) [$^2J$ ($^{119}Sn$-$^1H$) 18 Hz] 7.4-7.64 ppm (m, 15H, $Ph_3Sn$), 7.26 ppm corresponds to the NMR solvent, $CDCl_3$.

Disclosed are zeolitic materials that include a microporous crystalline framework substituted with one or more paired Lewis acid sites. Each of the one or more paired Lewis acid sites within the zeolitic material can comprise a first Lewis acid metal center and a second Lewis acid metal center. The first Lewis acid metal center and the second Lewis acid metal center can be separated by three or fewer atoms within the crystalline framework. For example, the first Lewis acid metal center and the second Lewis acid metal center can be separated by three atoms within the crystalline framework, or separated by one atom within the crystalline framework.

The first Lewis acid metal center and the second Lewis acid metal center can be separated by less than 10 Angstroms (e.g., less than 5 Angstroms, or less than 4 Angstroms), measured metal center to metal center. In certain embodiments, the first Lewis acid metal center and the second Lewis acid metal center are separated by from 2 to 4 Angstroms. In one embodiment, the first Lewis acid metal center and the second Lewis acid metal center are separated by from 2.5 to 3 Angstroms.

In some embodiments, each of the one or more paired Lewis acid sites in the zeolitic material can be defined by the formula below

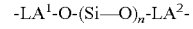
-LA$^1$-O-(Si—O)$_n$-LA$^2$- wherein LA$^1$ represents the first Lewis acid metal center; LA$^2$ represents the second Lewis acid metal center; and n is 0 or 1.

In some embodiments, n is 0, and each of the one or more paired Lewis acid sites in the zeolitic material can be defined by the formula below

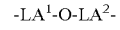
-LA$^1$-O-LA$^2$- wherein LA$^1$ represents the first Lewis acid metal center; and LA$^2$ represents the second Lewis acid metal center. In other embodiments, n is 1, and each of the one or more paired Lewis acid sites in the zeolitic material can be defined by the formula below -LA$^1$-O—Si—O-LA$^2$- wherein LA$^1$ represents the first Lewis acid metal center and LA$^2$ represents the second Lewis acid metal center.

In some embodiments, the first Lewis acid metal center and the second Lewis acid metal center can independently chosen from Sn, Hf, Zn, Zr, Ti, V, Ta, Ga, Ge, Nb, and Cr. In some embodiments, the first Lewis acid metal center and the second Lewis acid metal center can independently chosen from Sn, Hf, Zr, and Ge.

The first Lewis acid metal center and the second Lewis acid metal center can comprise the same metal or different metals. In some embodiments, the paired Lewis acid site can comprise a homodimer. In these instances, both the first Lewis acid metal center and the second Lewis acid metal center can comprise the same metal. For example, in one embodiment, the first Lewis acid metal center can be Sn and the second Lewis acid metal center can be Sn. In another embodiment, the first Lewis acid metal center can be Zr and the second Lewis acid metal center can be Zr.

In other embodiments, paired Lewis acid site can comprise a heterodimer. In these instances, the first Lewis acid metal center and the second Lewis acid metal center can comprise different metals. For example, in one embodiment, the first Lewis acid metal center can be Sn and the second Lewis acid metal center can be Zr.

The quantity (and by extension concentration) of paired Lewis acid sites included within the microporous crystalline framework of the zeolitic material can be varied. For example, in some embodiments, the molar ratio of paired Lewis acid sites to Si atoms in the zeolitic material can be at least 1:1000 (e.g., at least 1:900, at least 1:800, at least 1:750, at least 1:700, at least 1:600, at least 1:500, at least 1:400, at least 1:300, at least 1:250, at least 1:200, at least 1:100, at least 1:75, or at least 1:50). In some embodiments the molar ratio of paired Lewis acid sites to Si atoms in the zeolitic material can range between any of the values described above. For example, in some embodiments, the molar ratio of paired Lewis acid sites to Si atoms in the zeolitic material can be from 1:1000 to 1:50 (e.g., from 1:400 to 1:50, from 1:1000 to 1:500, from 1:1000 to 1:250, or from 1:400 to 1:100).

The zeolitic material can comprise suitable type of zeolite. For example, the zeolitic material can be of any suitable zeolite structural group (e.g., any suitable Nickel-Strunz classification). In some embodiments, the microporous crystalline framework can comprise BEA. In other embodiments, the microporous crystalline framework can comprise MFI.

Also provided are methods for preparing a zeolitic material that comprise a microporous crystalline framework isomorphously substituted with one or more paired Lewis acid sites. Methods for preparing these zeolitic materials can comprise combining, in aqueous solution, a silicon source, a paired Lewis acid monomer, and optionally a structure-directing agent to form a precursor gel; reacting the precursor gel under conditions effective to form a zeolitic precursor; and treating the zeolitic precursor to form the zeolitic material comprising the microporous crystalline framework isomorphously substituted with one or more paired Lewis acid sites.

As used herein, the terms "isomorphously substituted" and "isomorphous substitution" refer to the substitution of one element for another in a mineral without a significant change in the crystal structure. Elements that can substitute for each other generally have similar ionic radii and valence state. In one or more embodiments, a fraction of the silicon atoms are isomorphously substituted with a tetravalent metal. In other words, a fraction of the silicon atoms in the zeolitic framework material are being replaced with a tetravalent metal. Such isomorophous substitution does not significantly alter the crystal structure of the zeolitic framework material.

In some embodiments, step (i) can comprise combining, in aqueous solution, the silicon source, the paired Lewis acid monomer, and the structure-directing agent to form a precursor gel. In some cases, the structure-directing agent can comprise a quaternary ammonium hydroxide group. For example, the structure-directing agent can comprise a tetraalkyl ammonium hydroxide, such as tetraethyl ammonium hydroxide. The silicon source can comprise, for example, tetraethylorthosilicate.

In some embodiments, the paired Lewis acid monomer can be defined by the formula below

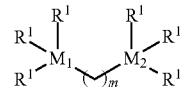

where $M_1$ and $M_2$ are independently chosen from Sn, Hf, Zn, Zr, Ti, V, Ta, Ga, Ge, Nb, and Cr; $R^1$ represents, independently for each occurrence, a halogen; and m is an integer from 1 to 5 (e.g., an integer from 1 to 3).

In some embodiments, m can be 1. In some embodiments, $R^1$ represents Cl.

In some embodiments, $M_1$ and $M_2$ can independently be chosen from Sn, Hf, Zn, Zr, Ti, V, Ta, Ga, Ge, Nb, and Cr. In some embodiments, $M_1$ and $M_2$ can independently be chosen from Sn, Hf, Zr, and Ge.

$M_1$ and $M_2$ can comprise the same metal or different metals. In some embodiments, the paired Lewis acid monomer can comprise a homodimer. In these instances, both $M_1$ and $M_2$ can comprise the same metal. For example, in one embodiment, $M_1$ can be Sn and $M_2$ can be Sn. In another embodiment, $M_1$ can be Zr and $M_2$ can be Zr.

In other embodiments, paired Lewis acid monomer can comprise a heterodimer. In these instances, $M_1$ and $M_2$ can comprise different metals. For example, in one embodiment, $M_1$ can be Sn and $M_2$ can be Zr.

In some embodiments, step (ii) can comprise incubating the precursor gel to hydrolyze the silicon source. This can comprise, for example, incubating the precursor gel for a period of from 12 hours to 72 hours at a temperature of from 20° C. to 40° C. In some embodiments, step (ii) can comprise heating the precursor gel in the presence of zeolite seed crystals to form the zeolitic precursor. Appropriate zeolite seed crystals can be selected in view of the desired morphology for the resulting zeolitic material. For example, in embodiments where the zeolitic material has a microporous crystalline framework that comprises BEA, step (ii) can comprise heating the precursor gel in the presence of BEA seed crystals to form the zeolitic precursor. In some embodiments, step (ii) can comprise heating the precursor gel in the presence of a fluoride source (e.g., $NH_4F$, $NH_4HF_2$, HF, or a combination thereof) to form the zeolitic precursor.

In some embodiments, step (iii) can comprise calcining the zeolitic precursor to form the zeolitic material comprising the microporous crystalline framework isomorphously substituted with one or more paired Lewis acid sites. For example, step (iii) can comprise heating the zeolitic precursor in air at a temperature of from 400° C. to 750° C. (e.g., at a temperature of about 550° C.). In some embodiments, step (iii) can comprise extracting the zeolitic precursor (e.g., by flowing an appropriate solvent through the zeolitic precursor) to form the zeolitic material comprising the microporous crystalline framework isomorphously substituted with one or more paired Lewis acid sites.

Zeolitic materials that include paired Lewis acid sites can exhibit improved catalytic activity (e.g., improved selectivity) relative to zeolites that include isolated Lewis acid sites. Accordingly, the zeolitic materials described herein can be used at heterogeneous catalysts in a wide variety of reactions that employ Lewis acid catalysts. For example, the zeolitic materials described herein can be used to catalyze the isomerization of sugars (e.g., the isomerization of glucose to fructose), Meerwein-Poondorf-Verley reductions (MPV), aldol condensations, Diels-Alder reactions, dehydrogenation reactions (e.g., the dehydrogenation of propane to propylene), and the synthesis of dimethylcarbonate from carbon dioxide.

The zeolitic materials described herein can also be used to catalyze selective oxidation reactions of organic compounds with hydrogen peroxide, organic peroxides or hydroperoxides. These selective oxidation reactions include: Baeyer-Villiger oxidations, oxidation of alkanes to alcohols or ketones; oxidation of alcohols to ketones; hydroxylation of aromatic compounds; epoxidation of olefins and; oxidation of thioethers to sulfoxides or sulphones.

The zeolitic materials described herein replace Lewis acid zeolite catalysts used in reactions such as those described in U.S. Pat. No. 8,729,256 to Moliner-Marin et al.; International Publication No. WO 2015/067654 to BASF SE; International Publication No. WO 2014/174416 to BASF SE and Tokyo Institute of Technology; International Publication No. WO 2014/197195 to California Institute of Technology, each of which is incorporated herein by reference in its entirety.

The catalytic processes described herein can be carried out either in a batch or continuous mode. In a batch mode, the reactants, either alone or in a solvent, can be combined in the presence of an effective amount of catalyst (a zeolitic material described herein). Generally, the weight percent of catalyst to substrate can vary from about 0.5 wt. % to about 50 wt. %. The contacting can carried out for an effective period of time to form the desired reaction product (e.g., from about 0.2 to about 24 hours).

Examples of continuous processes include fixed bed processes, continuous stirred tank processes, radial bed processes, etc. In such processes it can be advantageous, in order to minimize back pressure, to use the catalyst in particulate form such as pellets, extrudates, spheres, irregularly shaped particles, etc. The zeolites described herein can be formed into these shapes, either with or without a binder. If binders are used, any of the well known binders such as silica, alumina, silica-alumina, clays, etc. can be used.

By way of non-limiting illustration, examples of certain embodiments of the present disclosure are given below.

EXAMPLES

Example 1: Synthesis of Zeolites Including Paired Lewis Acid Sites

Overview

While many interesting enzymes, such as xylose isomerase, have catalytic sites consisting of pairs of Lewis acids, previously all such acid sites in zeolites were known to be isolated. Herein, zeolites that include paired Lewis acid sites are described. Paired site incorporation in the zeolite was confirmed using advanced spectroscopy methods, including DNP NMR. By creating a framework featuring paired Lewis acid sites, new dimensions are added to the synthetic capabilities of zeolites. Similar to enzymes that include paired Lewis acid sites, the paired site zeolite catalysts exhibit increased catalytic activity and selectivity relative to isolated site catalysts (e.g., for the isomerization of sugars).

Materials and Methods

Materials

All chemicals are used as received with no further purification with the exception of tetrahydrofuran (THF). Inhibitor free THF (Fisher, ACS grade) is dried using a MBraun Inc. MB-SPS DriSolv system. The following chemicals have been used: copper (II) acetate monohydrate (98.0-102.0%, Alfa Aesar), zinc granular (30 Mesh, J. T. Baker), glacial acetic acid (HPLC grade, J. T. Baker), triphenyltin chloride (95%, Acros Organic), dibromomethane (99% stab. with 50 ppm BHT, Alfa Aesar), tetraethylorthosilicate (98%, Acros Organics), tin (IV) chloride hydrate (98%, Alfa Aesar), tetraethylammonium hydroxide (35% by wt., Alfa Aesar, hydrochloric acid (36.5-38.00% by wt., reagent grade, J. T. Baker), hydrofluoric acid (52% by wt., Macron Fine Chemicals), ammonium hydroxide solution (28-30% by wt., Sigma Aldrich), anhydrous diethyl ether (Reagent grade, 7 ppm BHT, J. T. Baker), toluene (ACS grade, Macron Fine Chemicals), anhydrous sodium sulfate (ACS grade, Macron Fine Chemicals), hexanes (ACS grade, Macron Fine Chemicals), deuterated acetonitrile (XX), d-mannitol (USP grade, Amresco), d-glucose (USP grade, Fisher) deuterated (at C2 position) d-glucose (Cambridge Isotope Laboratories, Inc.), D-(+)-Mannose (99%, Alfa Aesar), D-fructose (99%, Alfa Aesar), deuterium oxide (99.9%, Macron Fine Chemicals), chloroform-d (99.8%, Isotopic, Beantown chemical), tetraphenyltin (97%, Aldrich), and boron nitride. DI water is obtained from a house supply, carefully monitored to produce Milli-Q quality water.

Synthesis of Bis(tripheneylstannyl)methane (4)

The two-step synthetic strategy used to prepare bis(tripheneylstannyl)methane (4) is illustrated in Scheme 1. First, triphenyltin chloride (1) was combined with dibromomethane (2) to produce (bromomethyl)triphenylstannane (3) using a LeGeoff Cu/Zn couple. Subsequently, compound (3) was combined with a triphenyltin chloride (3) using a Grignard to afford bis(tripheneylstannyl)methane (4). All procedures are executed using standard Schlenk techniques. Detailed procedures for both reactions are included below.

Scheme 1. Illustration of the two-step synthetic strategy used to prepare bis(tripheneylstannyl)methane (4). First, a Sn-C bond was formed using triphenyltinchloride and dibromomethane via LeGeoff's Cu/Zn couple. Subsequently, a second Sn-C bond was formed by coupling the (bromethyl) triphenylstannane with a second molecule of triphenyltinchloride via a Grignard reaction.

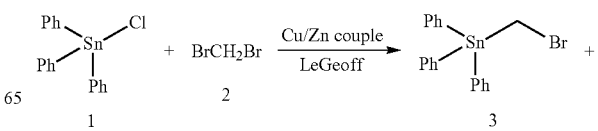

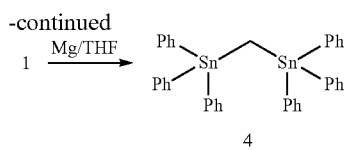

Synthesis of (Bromomethyl)triphenylstannane (3)

(Bromomethyl)triphenylstannane (3) was synthesized using two 100 mL 2-neck (14/20) round bottom (RB) flasks connected to each end to a Schlenk filter. The second neck of each RB was capped using a silicone rubber septum. The apparatus was purged with $N_2$ for 10-15 minutes and then flame dried under vacuum. The entire reaction was carried out under a nitrogen atmosphere. Copper acetate (26 mg; 0.13 mmol) was added to one RB. To this RB, glacial acetic acid (2.5 mL) was added and the mixture was stirred at 120° C. briefly. Once the temperature reached 120° C., metallic zinc (1.638 g; 25.05 mmol) was added. The mixture was stirred for 2-3 minutes at ~200 RPM until the color changes to reddish brown.

A separate 100 mL RB was filled with 12.5 mL glacial acetic acid and heated to 120° C. for washing the Zn—Cu couple. After the Zn—Cu couple was formed, the glacial acetic acid was removed via syringe and the couple was washed using 2.5 mL glacial acetic acid 5 times while still at 120° C. After these washings, the mixture was cooled to room temperature, and the Zn—Cu couple was washed 9 times using 5 mL dry THF each time at room temperature. The Zn—Cu couple was dried after the THF wash. Dry THF (2.2 mL) was added to the dried Zn—Cu couple and the temperature was increased to 40° C.

In another flame dried round bottom flask, a solution of 3 mL dibromomethane in 2.2 mL dry THF was prepared. A few drops (~0.05 mL) of dibromomethane solution was added via syringe to the Zn—Cu couple to activate the Zn—Cu couple. Activation was visualized by bubbling of reaction mixture or a color change to purple. Once the reaction was activated, 6.6 mL dry THF was added to the reaction mixture followed by the addition of the rest of dibromomethane solution. The reaction mixture was stirred until all the Zn dissolves (at least 4-5 h). After the reaction was complete, the reaction was quenched in an ice bath, and the set-up was flipped to filter the solution via the attached Schlenk filter into the second RB. The filtration was nitrogen assisted. A solution of triphenyltin chloride was prepared in a flame dried round bottom flask in dry THF by adding 2.25 g $Ph_3SnCl$ (5.84 mmol) in 3 mL dry THF. This solution was then added to the filtered reaction mixture dropwise at 40° C. The reaction mixture turned dark purple after few hours. The mixture was stirred for 6 h before stopping the reaction and purifying the product by liquid-liquid extraction.

Figure 1B:
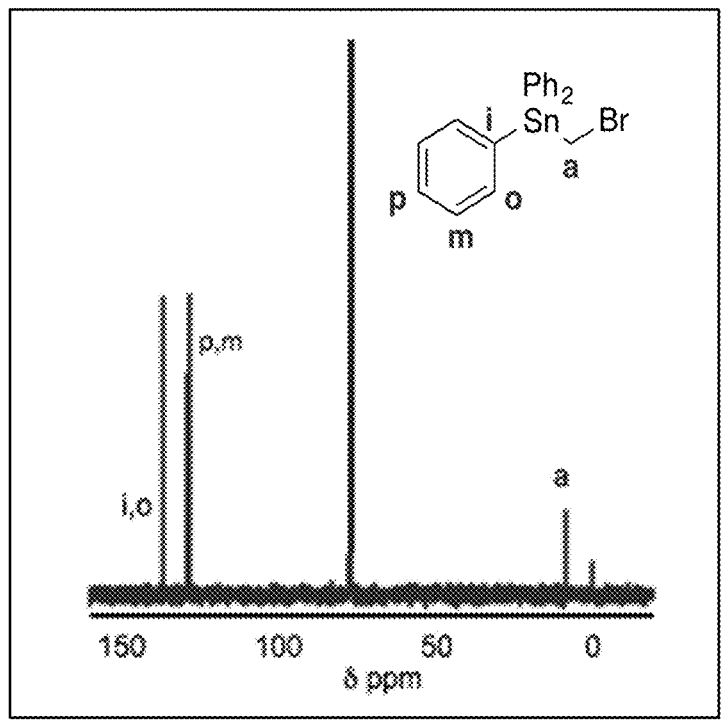
FIG. 1B shows the $^{13}C$ NMR spectra of (bromomethyl)triphenylstannane (3) in $CDCl_3$: δ 8.19 ppm (s, 2H, $CH_2$) 129.51 ppm ($C_p$), 128.74 ppm ($C_m$), 137.06 ppm ($C_o$) and 136.97 ppm ($C_i$).
Figure 1C:
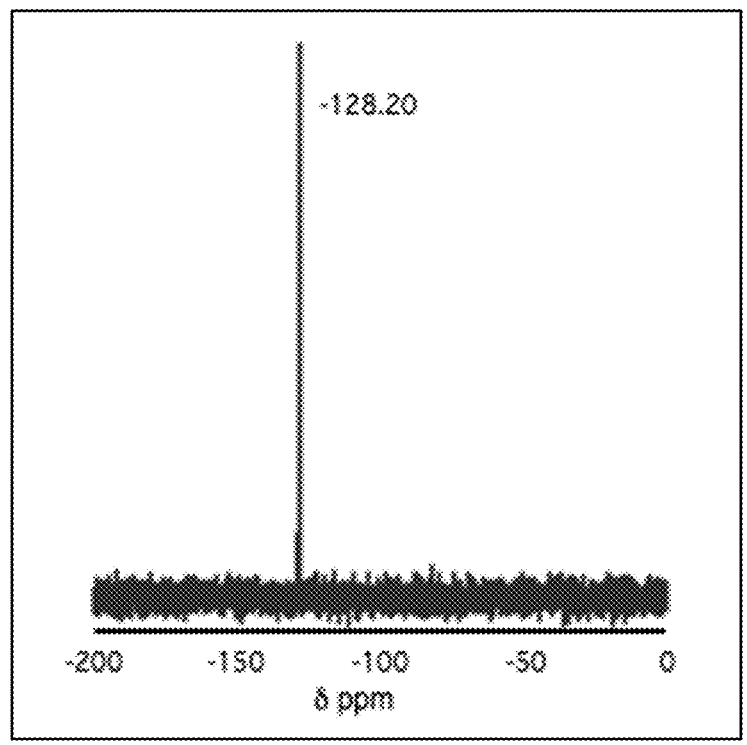
FIG. 1C shows the $^{119}Sn$ NMR spectra of (bromomethyl)triphenylstannane (3) in $CDCl_3$: δ −128.20 ppm.

The purification involved adding 20 mL toluene to the reaction mixture. This solution was extracted thrice using 40 mL of 5 wt % aqueous HCl solution. The final organic phase was dried using anhydrous sodium sulfate. The dried organic phase was concentrated by rotovapping the mixture at 55° C. until precipitation was observed. After all the toluene was removed, the product was purified by recrystallization in hexanes. The procedure yielded about 800 mg of pure product. The product was characterized by $^1H$ NMR, $^{13}C$ NMR, and $^{119}Sn$ NMR with $CDCl_3$ as the solvent. See FIGS. 1A-1C.

Synthesis of Bis(triphenylstannyl)methane (4)

The procedure is given for a basis of 1 g of 3. A 100 mL 2-neck round bottom flask connected to condenser was used for synthesis. The set-up was flame-dried under vacuum and then the reaction was carried out under nitrogen. One gram of magnesium turnings was added to the RB. The magnesium was stirred using a Teflon stirrer overnight at 120° C. (1200-1400 RPM). Two separate flame dried 25 mL RB flasks were used to prepare 3 (1 g) and $Ph_3SnCl$ (1; 0.784 g) solutions in dry THF. Dry THF was added to the round bottom flasks: 2 mL to Mg, 1.5 mL to 3, and 1.5 mL to 1. A few drops of solution containing 3 were added to the Mg at 40° C. and the reaction was allowed to activate. The activation was characterized by bubbling and a color change to dark grey/black. Once the reaction was activated, the entire solution of 3 was added and the reaction mixture was stirred for 2-4 h. After the reaction was complete, the reaction mixture was quenched in an ice bath. The solution of 1 was then added dropwise at 0° C. After the addition was complete, the reaction was heated to 80° C. The reaction mixture turned to greenish black color as it was allowed to stir overnight. The final reaction mixture has a dark grey-black color. The reaction mixture was then quenched in an ice bath. The reaction mixture was diluted by addition of diethyl ether (40-50 mL). This step was important for the extraction of entire product in the organic phase. The unreacted magnesium was scavenged by dropwise adding 5 wt % aqueous HCl at 0° C. Approximately 10-12 mL HCl solution was added.

Figure 2A:
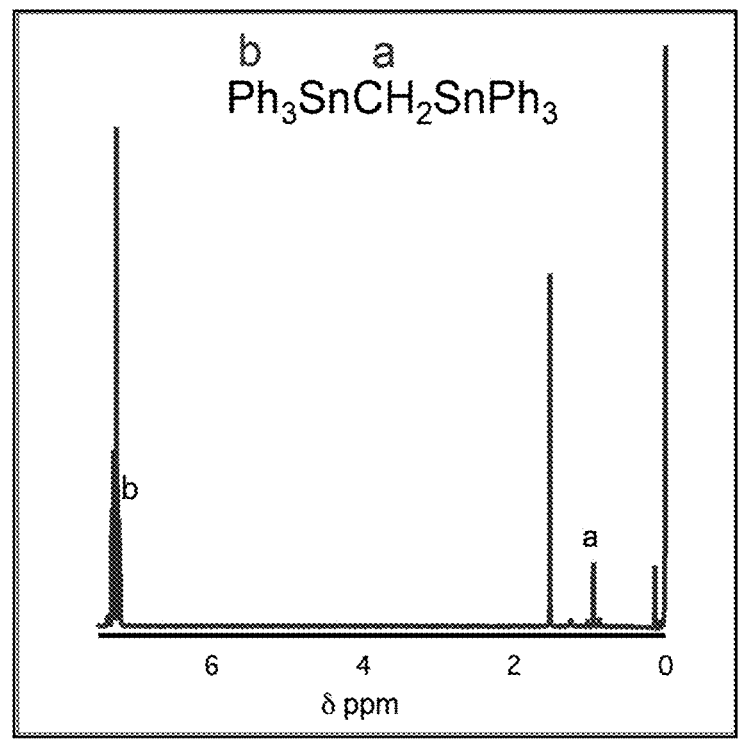
FIG. 2A shows the $^1H$ NMR spectra of bis(triphenylstannyl)methane (4) in $CDCl_3$: δ 0.96 ppm (s, 2H, $CH_2$) [$^2J$ ($^{119}Sn$—C-$^1H$) 66 Hz] 7.21-7.32 ppm (m, 15H, $Ph_3Sn$), 7.26 ppm corresponds to the NMR solvent, $CDCl_3$.
Figure 2B:
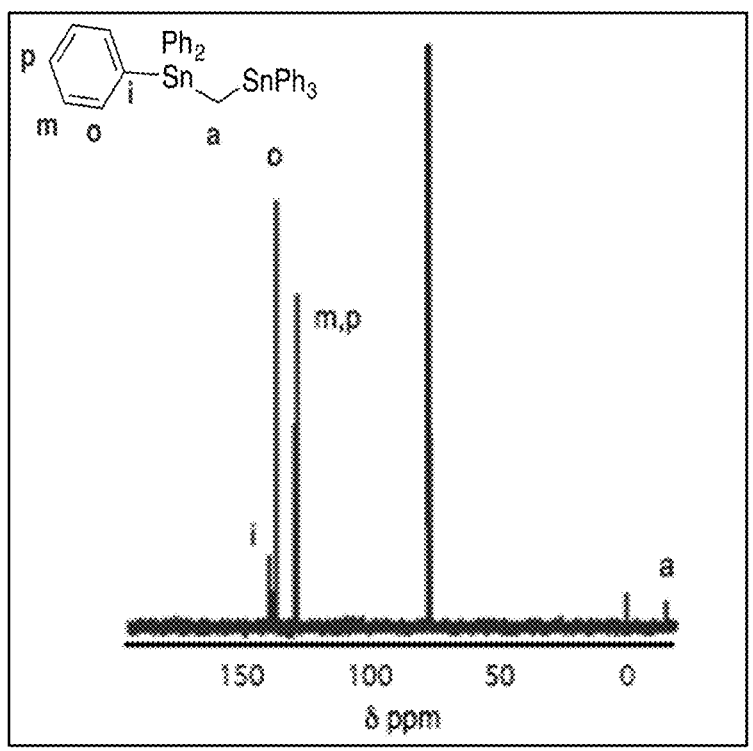
FIG. 2B shows the $^{13}C$ NMR spectra of bis(triphenylstannyl)methane (4) in $CDCl_3$: δ −16.23 ppm (s, 2H, $CH_2$) 128.78 ppm ($C_p$), 128.36 ppm ($C_m$), 136.89 ppm ($C_o$) and 139.33 ppm ($C_i$).
Figure 2C:
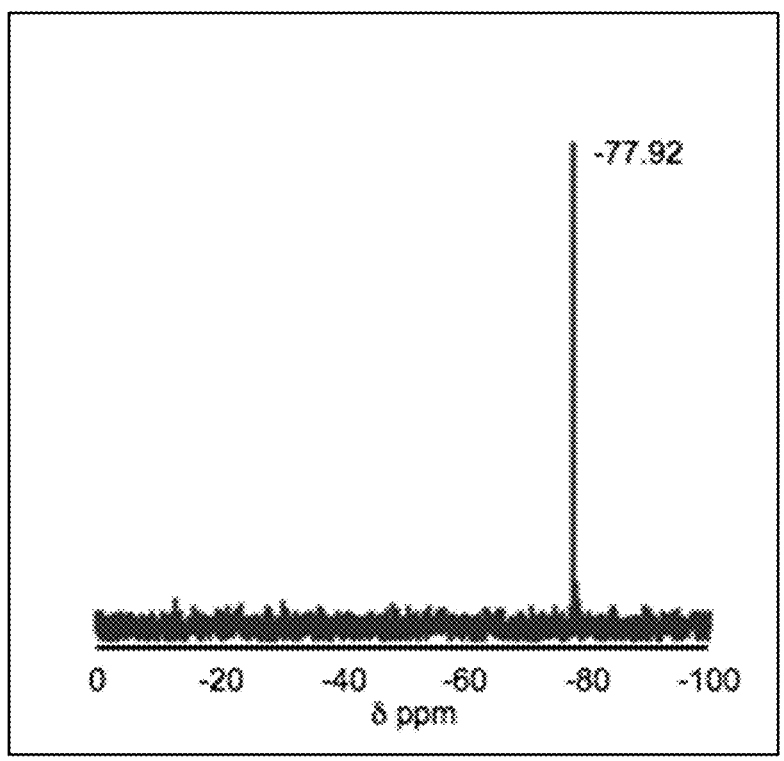
FIG. 2C shows the $^{119}Sn$ NMR spectra of bis(triphenylstannyl)methane (4) in $CDCl_3$: δ −77.92 ppm.

The next step involved separation of product by liquid-liquid extraction. The organic phase was washed thrice by DI water to remove all the HCl from organic phase. The organic phase was dried by adding anhydrous sodium sulfate. The dried organic phase was filtered and then concentrated by rotovapping the mixture at room temperature until precipitation was observed. This crude product was recrystallized using ethanol at 90° C. (~3-5 mL ethanol was used). The recrystallized product was filtered and washed with small amount of cold ethanol. The product (4) was characterized by $^1H$ NMR, $^{13}C$ NMR, and $^{119}Sn$ NMR with $CDCl_3$ as the solvent. See FIGS. 2A-2C.

Synthesis of Bis(trichlorostannyl)methane (5)

Figure 3:
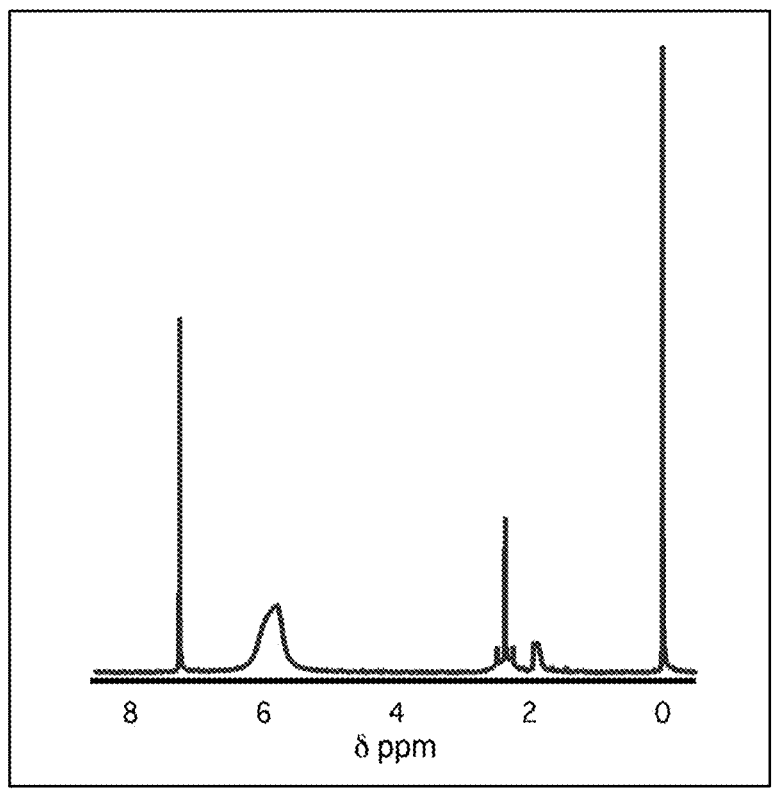
FIG. 3 illustrates the $^1H$ NMR spectrum of bis(trichlorostannyl)methane (5) in $CDCl_3$. δ 2.37 ppm (s, 2H, $CH_2$) [$^2J$ ($^{119}Sn$-$^1H$) 96 Hz] correspond to methylene bridge in (5). δ 0.0 ppm and 7.26 ppm are peaks from tetramethylsilane (internal standard) and chloroform. The remaining peaks are attributed to residual water and HCl from the reaction mixture.

Bis(trichlorstannyl)methane (5) was the precursor added to the zeolite synthesis gel. The synthetic strategy used to prepare bis(trichlorstannyl)methane (5) is illustrated in Scheme 2. For different Sn:Si (i.e., 400:1, 200:1, 100:1), the amount of bis(triphenylstannyl)methane required was different. The required amount of bis-(triphenylstannyl)methane was heated at 60° C. with a 10-fold excess of concentrated HCl for ~40 hours to afford bis(trichlorostannyl) methane (5). The reaction mixture was then used as is for paired Sn-β synthesis. The $^1H$ NMR in FIG. 3 shows that the concentrate did possess the methylene bridged protons characteristic of bis(trichlorostannyl)methane (singlet at δ 2.37 ppm with 2J $^{119}Sn$-$^1H$=96 Hz).

Scheme 2. Illustration of the synthetic strategy used to prepare bis(trichlorstannyl) methane (5). A chloro-exchange process was used to convert bis(triphenylstannyl)methane (4) into bis(trichlorostannyl) methane (5). The desired amount of precursor was added to a concentrated HCl solution containing a 10-fold excess of HCl.

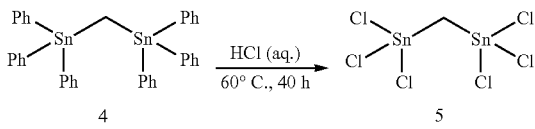

Alternative Strategies for the Preparation of Precursors

In some cases, the precursor may be unstable during the chloro-exchange process. If desired, alternative synthetic strategies that employ milder reaction conditions may be used to prepare a suitable precursors for the preparation of zeolite gels. An example is occurred in Scheme 3 below.

Scheme 3. Illustration of the synthetic strategy that can be used to prepare precursors to be added to a zeolite synthesis gel.

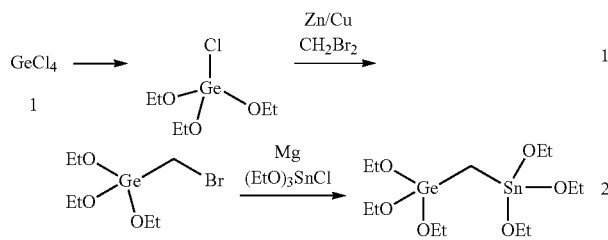

An example alternative method to prepare precursors, such as a Sn—Ge heterodimer precursor, can involve alkoxide intermediates instead of phenyl intermediates to avoid the phenyl- to chloro-exchange conditions. This procedure can first involve converting germanium tetrachloride to triethoxy germanium chloride through adding ethanol and a bulky base to quench the HCl that is generated. This intermediate can then be converted to (bromomethyl)triethoxygermane using a zinc/copper couple with dibromomethane described previously for the synthesis of the tin dimer precursor. This intermediate can then be coupled using a Grignard reaction with triethoxy tin chloride to produce 4,4,6,6-tetraethoxy-3,7-dioxa-4-germa-6-stannanonane.

This precursor can be added to a zeolite crystallization gel to produce the material with paired Sn—Ge metal centers. As an alternative, the same precursor could also be produced through reaction a triethoxy tin chloride with a zinc/copper couple to produce a (bromomethyl)triethoxystannane intermediate that could then be coupled with triethoxy germanium chloride through a Grignard reaction to produce the desired precursor. While ethoxy groups are described in this reaction scheme, alternative alkoxy species should function similarly.

Synthesis of isolated Sn-β

Tetraethylorthosilicate (TEOS; 98%, Aldrich; 3.06 g (0.015 mol)) was combined with 3.31 g tetraethyl ammonium hydroxide (TEAOH) (35 wt % aqueous solution, TEA$^+$=0.008 mol), adding TEOS dropwise. The mixture was stirred for 60-90 min until a single phase solution was formed. In a separate vial, 0.051 g SnCl$_4$·5H$_2$O (0.00015 mol) was added to 0.2 mL DI water. This solution was added to the TEOS/TEAOH mixture. The mixture was allowed to hydrolyze overnight (20-24 hours). The hydrolyzed mixture was rotovapped to remove ethanol and some water, adding 5 g of distilled water after each rotovapping in order to remove the ethanol completely. 0.16 g DI water was added to the final synthesized gel. The synthesis gel was then transferred to reactor Teflon-lined 44 mL acid-digestion vessel (Parr Inst. Comp.). 0.27 mL HF (51 wt % aqueous solution) and 44 mg of calcined Si-β seeds were added to the synthesis gel and the mixture was stirred using Teflon rod. The final gel composition was 1 SiO$_2$/0.01Sn/0.54F$^-$/0.54 TEA/7.5 H$_2$O. The acid digestion vessel was sealed and placed in a preheated oven at 140° C. with rotation at 35 RPM. The material was allowed to crystallize for 30 days. All materials were filtered and washed with 250 mL DI H$_2$O. The materials were then dried in an oven at 80° C. overnight. The dried materials were then calcined in air at 550° C. for 10 h to remove the structure directing agent.

Synthesis of Paired Sn-β

Paired Sn-β was synthesized in a similar way as isolated Sn-β. However, in case of paired Sn-β, the tin source was the solution of bis(trichlorostannyl)methane (5) in aqueous HCl. To quench the excess HCl in the solution of 5, NH$_4$OH was simultaneously added along with the bis(trichlorostannyl) methane solution to the TEOS/TEAOH mixture. The synthesis gel was then allowed to hydrolyze for 20 h. The same procedure as isolated Sn-β was used after hydrolysis. However, the paired Sn-β required more time to crystallize as compared to isolated. Therefore, paired Sn-β was allowed to crystallize for 10-120 days. The time required for crystallization was found to be a product of the Si/Sn ratio: higher Sn content required longer crystallization times. All materials were filtered and washed with 250 mL DI H$_2$O. The materials were then dried in an oven at 80° C. overnight. For materials used for catalytic testing, the dried materials were then calcined in air at 550° C. for 10 h to remove the SDA.

Material Characterization

The materials were characterized using a battery of standard techniques, including powder X-ray diffraction (pXRD), nitrogen physisorption, scanning electron microscopy (SEM), diffuse reflectance ultraviolet-visible spectroscopy (DR-UV-vis), Fourier Transform Infra Red (FTIR) spectroscopy, X-ray Absorption Spectroscopy (XAS), and solid state NMR.

Powder X-Ray Diffraction

Figure 4A:
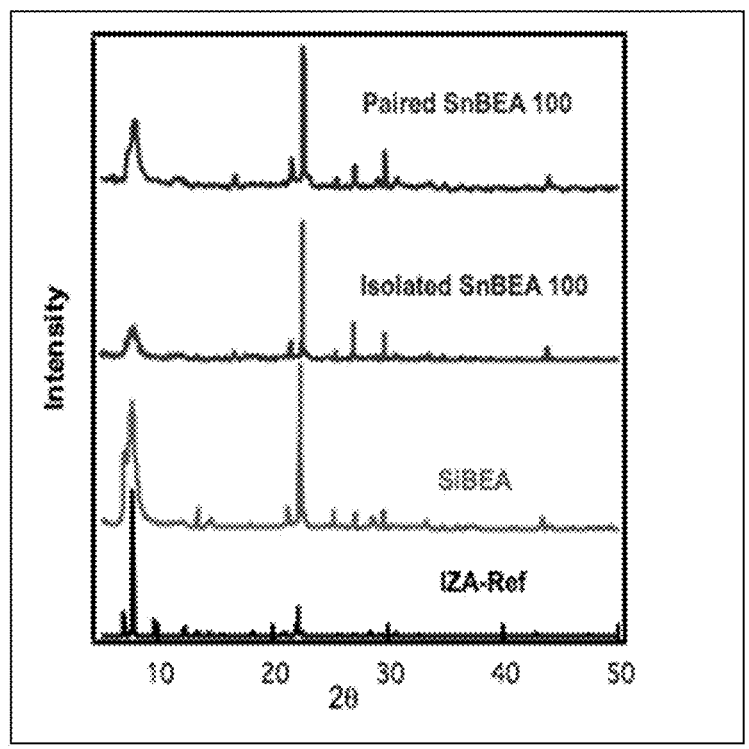
FIG. 4A shows the powder X-ray diffraction (pXRD) patterns of synthesized SiBEA, isolated SnBEA (Si/Sn=100), and paired SnBEA (Si/Sn=100) along with the International Zeolite Association (IZA)'s reference for BEA.
Figure 4B:
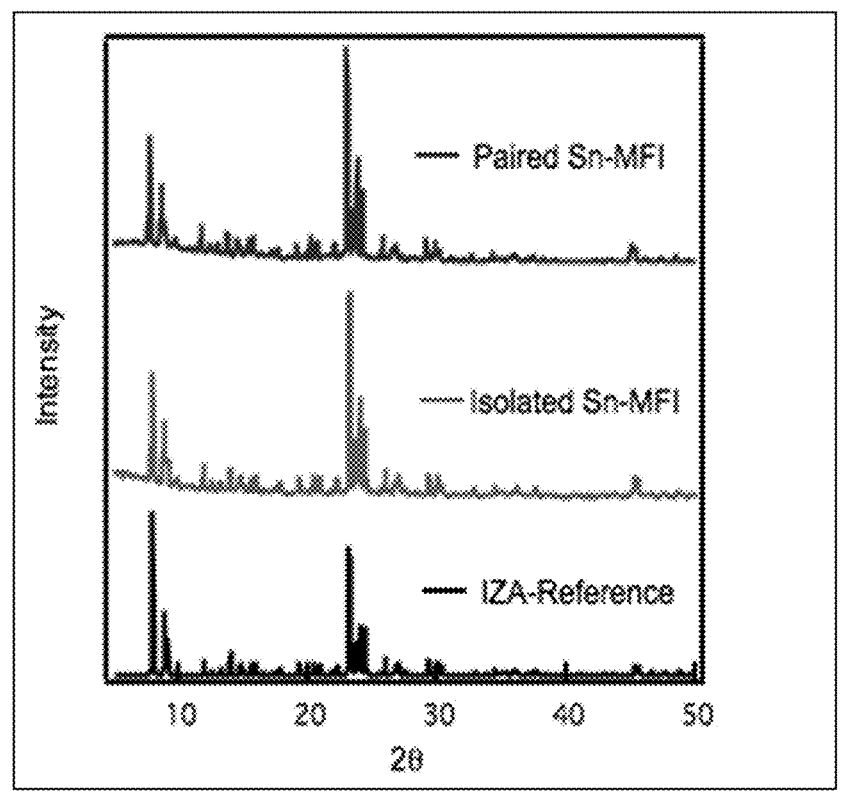
FIG. 4B shows the pXRD pattern of synthesized isolated Sn-MFI (Si/Sn=200) and paired Sn-MFI (Si/Sn=200) along with the International Zeolite Association (IZA)'s reference for MFI.

The crystallinity of synthesized samples was determined by powder X-ray diffraction (pXRD) collected at room temperature using Bruker X-ray powder diffractometer. The diffraction data is collected in standard reflection mode using monochromatic Cu K$_{\alpha 1}$ radiation (λ=1.54 Å) at 40 kV and 50 mA. The pXRD patterns for pure Si-BEA, isolated Sn-BEA, and paired Sn-BEA are shown in FIG. 4A. The pXRD patterns for Sn-MFI (Si/Sn=200) and paired Sn-MFI (Si/Sn=200) are shown in FIG. 4B.

Nitrogen Physisorption

Figure 5:
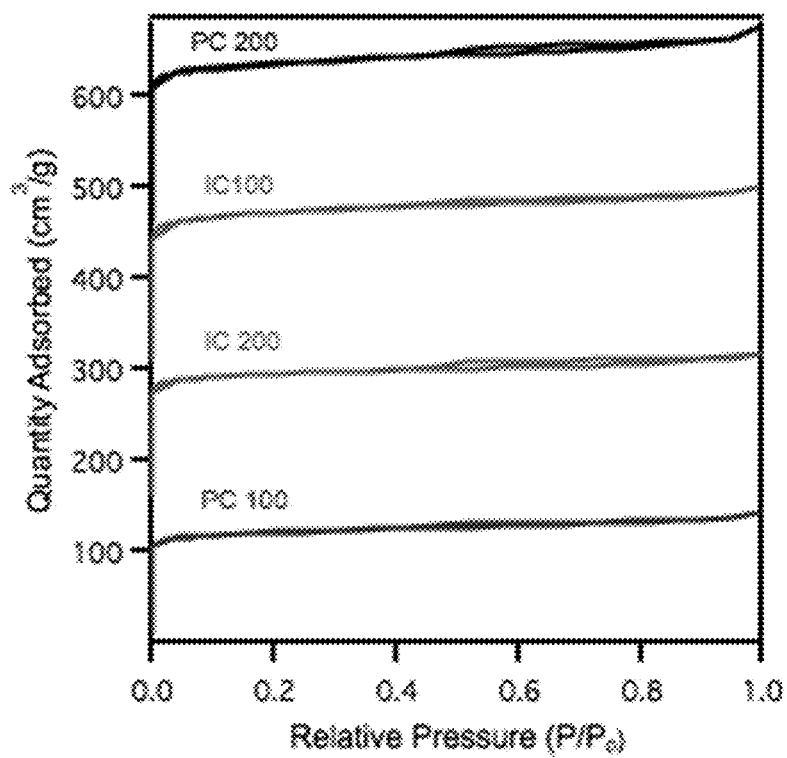
FIG. 5 shows $N_2$ physisorption plots of isolated Sn BEA (Si/Sn=100 and 200) and paired Sn BEA (Si/Sn=100 and 200). Both materials exhibited type (IV) characteristics. Isotherms are offset by 150 $cm^3/g$ in y-direction for better visualization.

The textural properties of the materials are analyzed using Micromeritics 3Flex surface characterization analyzer. All samples displayed reversible adsorption-desorption isotherms, which is consistent with isotherm behavior for microporous materials. The isotherms for pure Si-BEA, isolated Sn-BEA, and paired Sn-BEA are shown in FIG. 5. The t-plot micropore volume and micropore area for isolated Sn BEA (Si/Sn=100 and 200) and paired Sn BEA (Si/Sn=100 and 200) are shown in Table 1.

TABLE 1 t-plot micropore volume and micropore area for isolated Sn BEA (Si/Sn = 100 and 200) and paired Sn BEA (Si/Sn = 100 and 200).

| Sample | t-plot Micropore Volume (cm$^3$/g) | Micropore area (m$^2$/g) |
|---|---|---|
| PC 100 | 0.16 | 314 |
| IC 100 | 0.22 | 420 |
| PC 200 | 0.24 | 477 |
| IC 200 | 0.19 | 373 |

Elemental Analysis

The elemental analyses were performed by Galbraith laboratories to determine the actual Si and Sn content in isolated samples. Using inductively coupled plasma optical emission spectrometry (ICP-OES), Si and Sn weight percentages in isolated and paired Sn-BEA can be measured.

Scanning Electron Microscopy (SEM)

Figure 6:
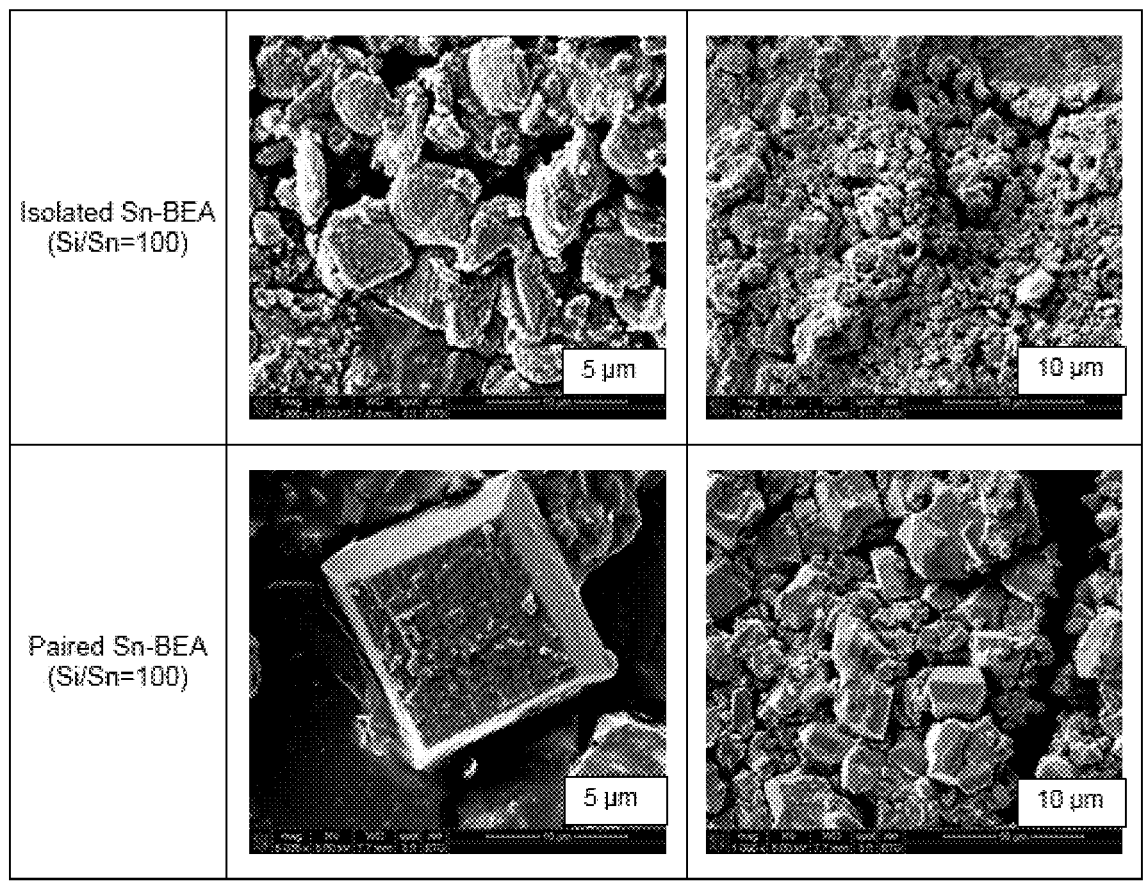
FIG. 6 shows SEM micrographs of Isolated Sn-BEA (Si/Sn=100) and Paired Sn-BEA (Si/Sn=100). The images were taken at 5 μm and 10 μm magnification. Both isolated and paired Sn-β display a broad distribution of particle size. Both Isolated and Paired Sn-β display a capped bipyramidal morphology with intergrowth.

Particle morphology and size was determined using FEI Nova 400 NanoSEM scanning electron microscopy (SEM). Briefly, dried samples were dispersed in 300 µL and then coated on carbon conductive tape using a micropipette. The sample was sputtered at 17 mA for 60 s with a gold-palladium alloy using Cressington 108 Sputter coater before analysis. Example SEM micrographs of Isolated Sn-BEA (Si/Sn=100) and Paired Sn-BEA (Si/Sn=100) are illustrated in FIG. 6.

Diffuse Reflectance UV-Vis Spectroscopy (DR-UV-Vis)

Figure 7A:
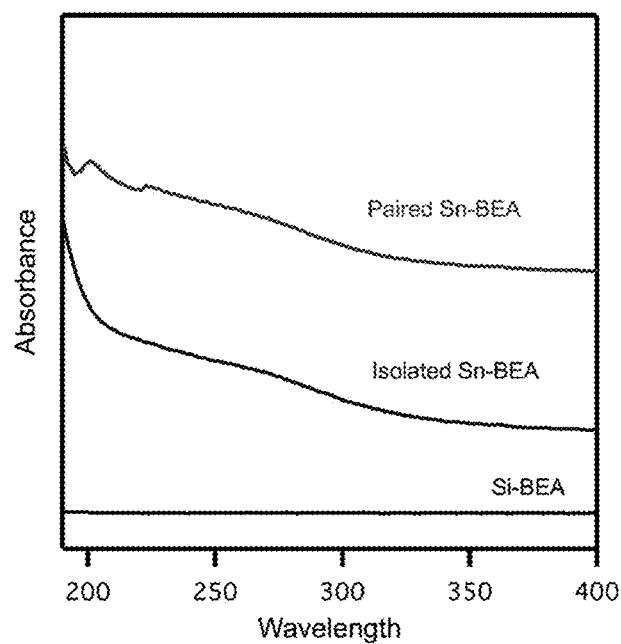
FIG. 7A illustrates diffuse reflectance UV-Vis spectra for isolated and paired Sn-BEA synthesized with Si/Sn 100. The spectra was collected after dehydrating the sample at 250° C. for 30 min using Si-BEA as 100% reflectance standard.
Figure 7B:
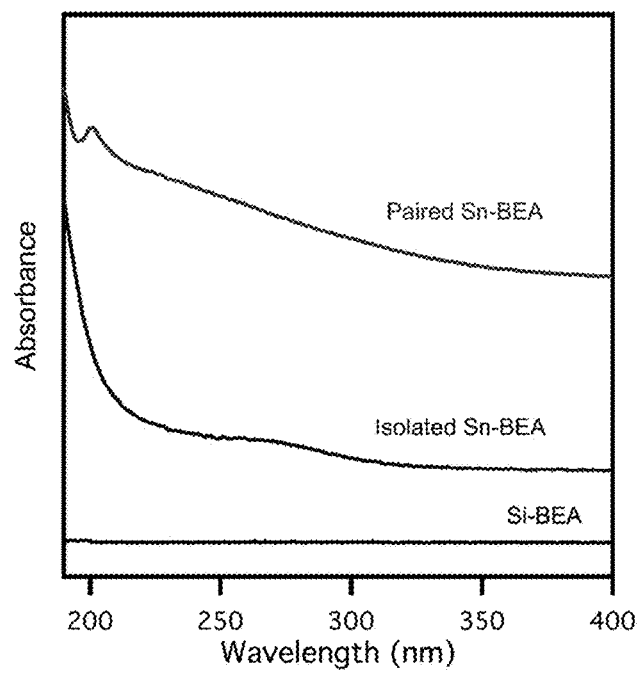
FIG. 7B illustrates diffuse reflectance UV-Vis spectra for isolated and paired Sn-BEA synthesized with Si/Sn 200. The spectra was collected after dehydrating the sample at 250° C. for 30 min using Si-BEA as 100% reflectance standard.

The DR-UV-vis spectra were collected on Evolution 300 UV-Vis spectrometer with a resolution of 2 nm at a rate of 10 $nms^{-1}$ with Si-β as background standard. The hydration experiment was performed using a Harrick Praying Mantis in-situ diffuse reflectance cell. The sample was first dehydrated at 250° C. for 30 min under dry nitrogen. The temperature was reduced to 30° C. and the material was exposed to wet $N_2$ for 5 min to rehydrate the material. The material was again dehydrated at 250° C. for 30 min to remove the $H_2O$. Spectra were collected at every step and also before and after the entire treatment at 25° C. Example spectra are illustrated in FIGS. 7A and 7B.

Diffuse Reflectance FTIR Spectroscopy (DRIFTS)

The location of the Sn atoms in the isolated and paired materials was characterized with diffuse reflectance Fourier transform IR spectroscopy (DRIFTS) using deuterated acetonitrile as the probe molecule. Deuterated acetonitrile is a Lewis base probe molecule that can exhibit different binding strength for closed and open framework Sn sites. The difference in binding strength allows the detection of both types of framework Sn sites. The IR spectra were collected on a Nicolet iS50 spectrometer with MCT-A liquid nitrogen cooled detector (32 scans at 2 $cm^{-1}$ resolutions are collected for every spectrum using the bare material (without $CD_3CN$ exposure) as the background reference.

Figure 8:
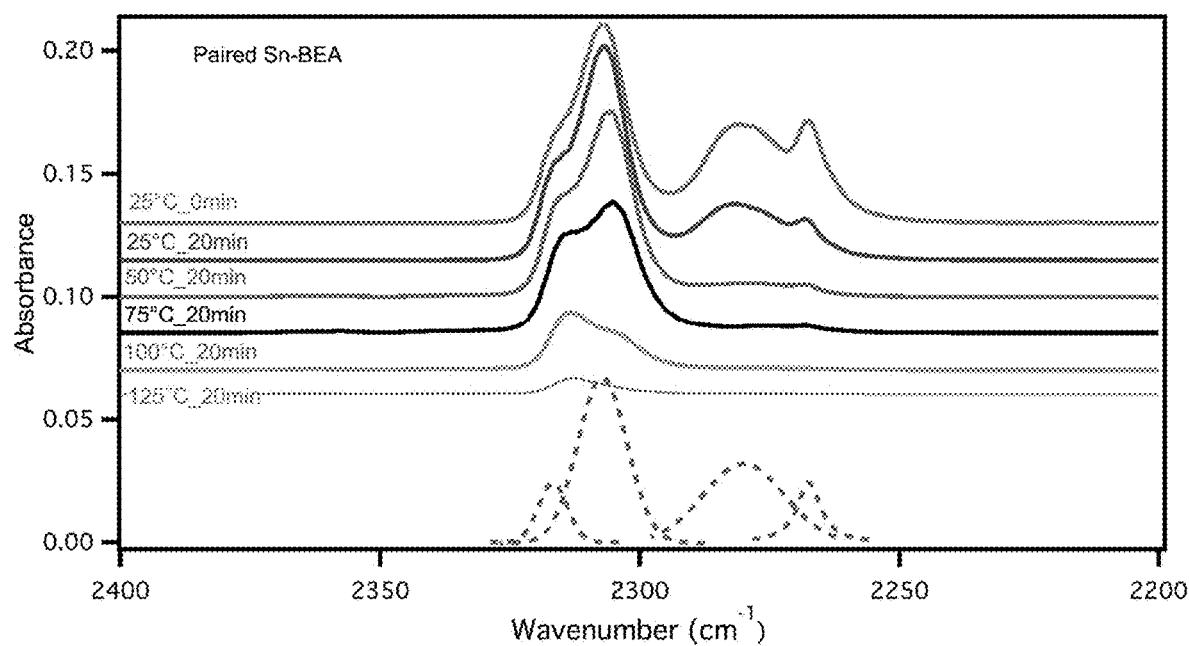
FIG. 8 illustrates diffuse reflectance IR spectra for Paired Sn-BEA (Si/Sn=100) collected after dehydrating the sample at 500° C. for 60 min. The sample was dosed with deuterated acetonitrile. Solid curves display the spectrum collected at different temperatures as the acetonitrile is desorbed. The dotted curve represents the deconvoluted spectrum showing four peaks at (1) 2317 cm$^{-1}$ (Open Sn-site), (2) 2307 cm$^{-1}$ (Closed Sn-site), (3) 2280 cm$^{-1}$ (Silanol adsorption), and (4) 2267 cm$^{-1}$ (Physisorption).
Figure 9:
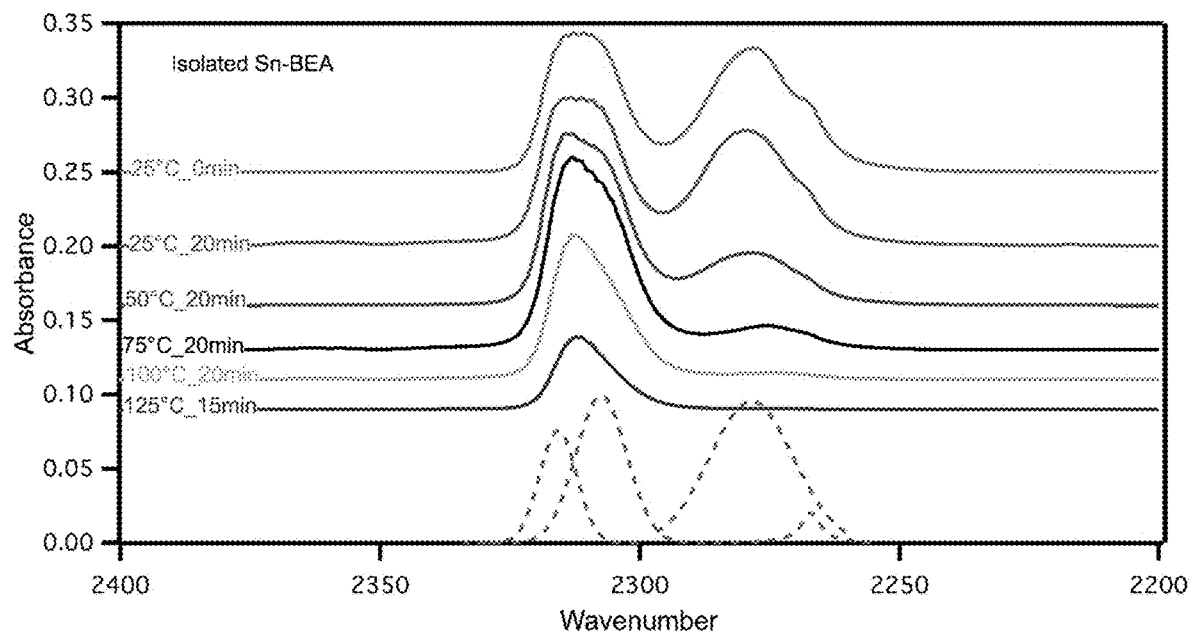
FIG. 9 illustrates diffuse reflectance IR spectra for Isolated Sn-BEA (Si/Sn=100) collected after dehydrating the sample at 500° C. for 60 min. The sample was dosed with deuterated acetonitrile. Solid curves display the spectrum collected at different temperatures as the acetonitrile is desorbed. The dotted curve represents the deconvoluted spectrum showing four peaks at (1) 2317 cm$^{-1}$ (Open Sn-site), (2) 2307 cm$^{-1}$ (Closed Sn-site), (3) 2280 cm$^{-1}$ (Silanol adsorption), and (4) 2267 cm$^{-1}$ (Physisorption).
Figure 10A:
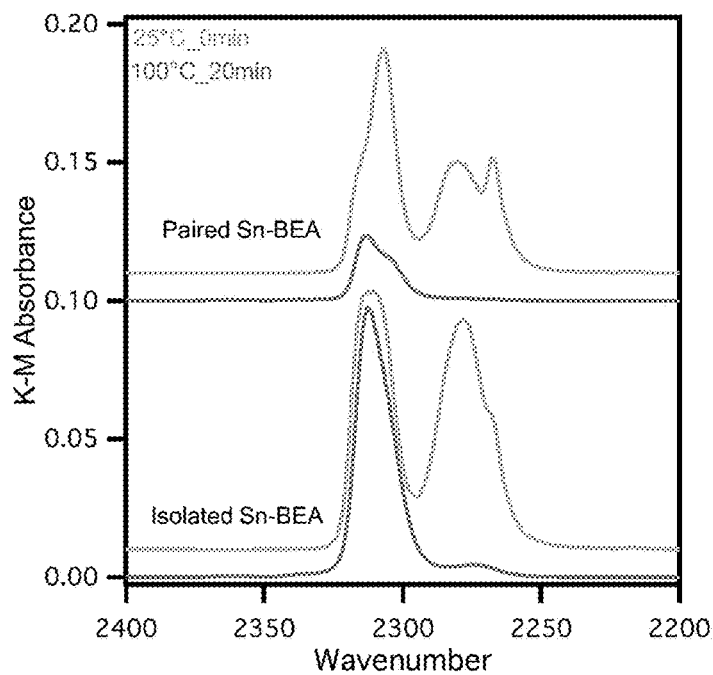
FIG. 10A illustrates a comparison of diffuse reflectance IR spectra with acetonitrile as the probe of isolated and paired Sn-BEA with Si/Sn 100. The spectra collected immediately after dosing and after desorption at 100° C. are compared for both Isolated and Paired Sn-BEA. The paired Sn-BEA preferentially adsorbed on the framework Sn sites as compared to the silanol adsorption and physisorption.
Figure 10B:
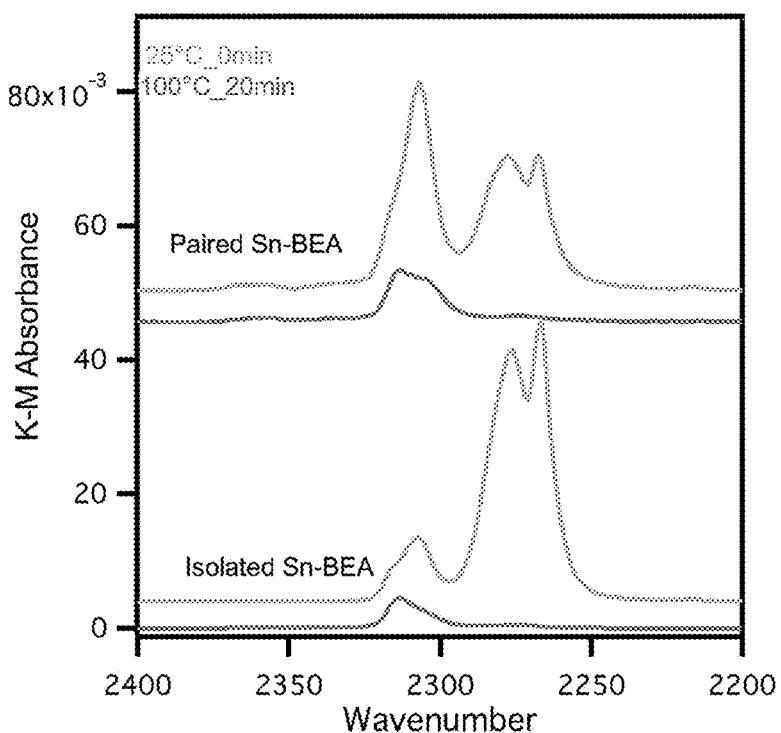
FIG. 10B illustrates a comparison of diffuse reflectance IR spectra with acetonitrile as the probe of isolated and paired Sn-BEA with Si/Sn 200. The spectra collected immediately after dosing and after desorption at 100° C. are compared for both Isolated and Paired Sn-BEA. The paired Sn-BEA preferentially adsorbed on the framework Sn sites as compared to the silanol adsorption and physisorption.

Briefly, the materials were first degassed in-situ under $N_2$ flow at 500° C. for 60 minutes. The temperature was then reduced to 25° C. after degassing, and the sample was dosed with an acetonitrile pulse at room temperature. The weakly physisorbed acetonitrile was then desorbed under nitrogen. The material was then heated to 125° C. with 25° C. steps, maintaining temperature for 20 min at every step under nitrogen. Spectra were collected at every 25° C. temperature step. Diffuse reflectance IR spectra for Paired Sn-BEA (Si/Sn=100) and Isolated Sn-BEA (Si/Sn=100) are shown in FIGS. 8 and 9, respectively. FIG. 10A and FIG. 10B illustrates a comparison of diffuse reflectance IR spectra with acetonitrile as the probe of isolated and paired Sn-BEA with Si/Sn 100 and Si/Sn 200, respectively.

X-Ray Absorption Spectroscopy (XAS) Experiments

XAS experiments were performed at Argonne National Labs to confirm the presence of paired Sn-sites in the synthesized zeolites. These studies involved X-ray absorption near-edge spectroscopy (XANES), which confirmed the formal oxidation state of the tin-atoms to be +4. XAS data was also used to obtain the extended x-ray absorption fine-structure (EXAFS) spectra. This data could be used to determine at least the first coordination sphere (distances and bonding partners) and possibly even the second coordination sphere of tin atoms in the zeolites.

Figure 11:
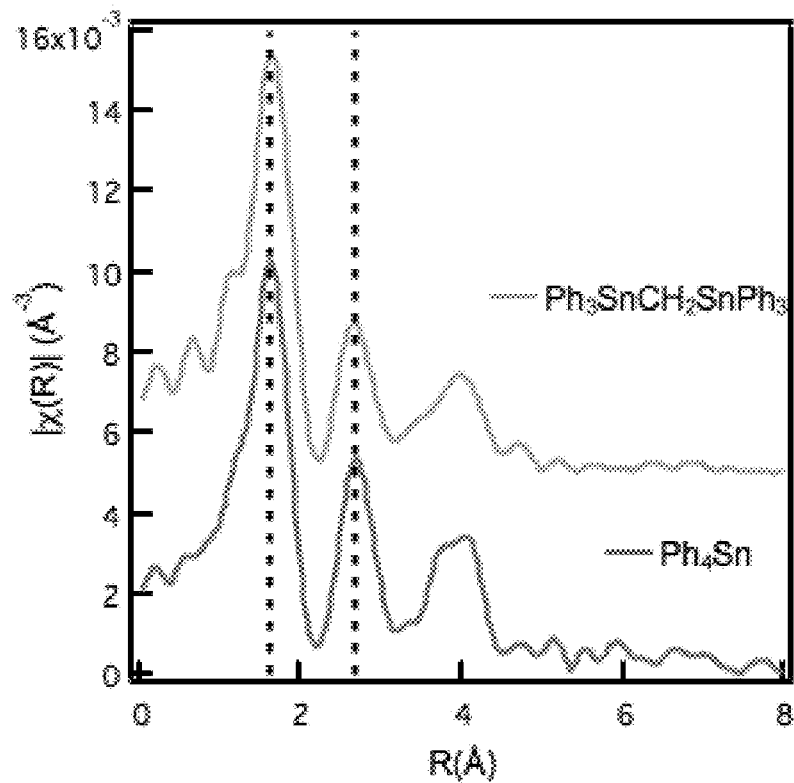
FIG. 11 shows a comparison of the EXAFS of tetraphenyltin (Ph$_4$Sn) and bis(triphenylstannyl)methane (4). No difference in the position of the major peaks between the two was observed. This suggests that EXAFS may not be able to be used to differentiate between isolated Sn BEA and paired Sn-BEA with Sn atoms separated by a methylene bridge. Note: spectra of 4 was off-set by χ=0.01

In this case, using EXAFS to differentiate between paired sites and isolated sites based on the first co-ordination sphere was difficult because of the similar electron scattering properties of O and C atoms. However, the second coordination sphere should provide a means for differentiating between paired sites and isolated sites, because one would expect to observe a tin atom in the second coordination sphere of every tin atom in the paired material. To determine whether EXAFS can be used to identify the presence of a pair of tin atoms spaced by a methylene bridge, the EXAFS spectra of tetraphenyltin ($Ph_4Sn$) and (4) were compared. For these spectra, boron nitride was used as a diluent. The results are shown in FIG. 11. As shown in FIG. 11, all major peaks for the monomeric tetraphenyltin and the dimeric tin species (4), with the tin atoms separated by a methylene bridge, were observed at identical positions. This suggests that EXAFS may not be able to be used to differentiate between the isolated and paired Sn-BEA to demonstrate the existence of paired Sn atoms at adjacent T-positions.

Figure 12:
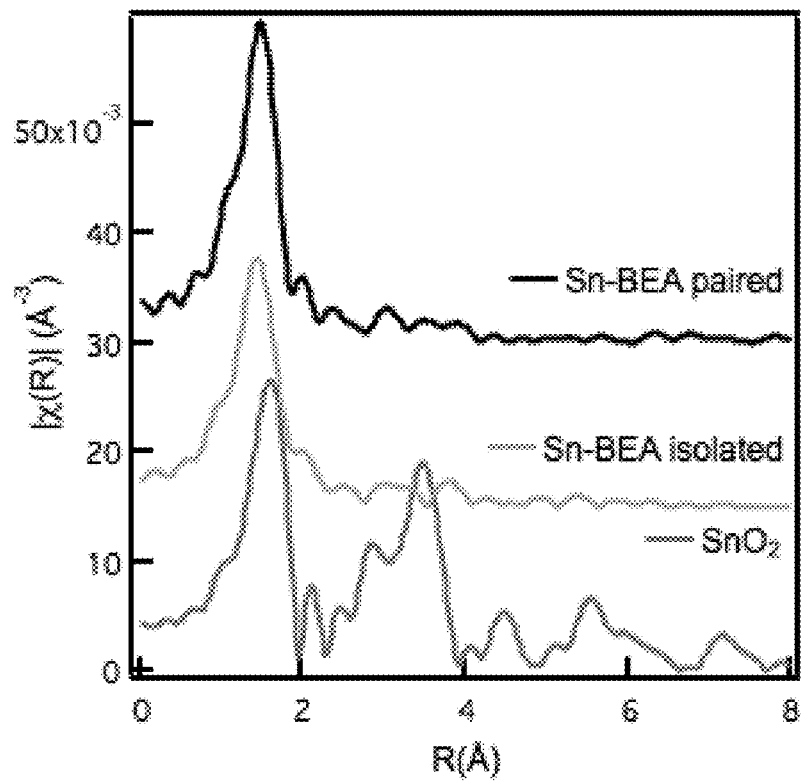
FIG. 12 shows a comparison of the EXAFS of SnO$_2$, isolated Sn-BEA, and paired Sn-BEA. The position of the first peak in the spectra denotes averaged bonding distance between Sn and its bonding partners. Shorter bonding distances for Sn in paired and isolated BEA as compared to those in SnO$_2$ indicated the presence of framework tin in both BEA materials. A slight difference in the bonding distances between paired and isolated Sn-BEA was also observed. Note: spectra of Sn-BEA isolated and Sn-BEA paired were off-set by χ=0.015 and 0.030 respectively.

Sn-BEA paired (no diluent), Sn-BEA isolated (no diluent) and $SnO_2$ (boron nitride as diluent) were also analyzed using EXAFS. The results are shown in FIG. 12. The location of the first peak in EXAFS depends on the averaged bond-lengths of all bonds formed by the excited Sn atom. As shown in FIG. 12, shorter bond-distances for paired Sn-BEA and isolated Sn-BEA were observed when compared to bulk $SnO_2$. This corroborated the DR-UV-Vis evidence that framework Sn atoms exist in isolated and paired Sn-BEA. There was a slight difference in the location of the first peak for the isolated and paired Sn-BEA too. However, that may not be sufficient to confirm the presence of paired Sn atoms in paired Sn-BEA.

Catalytic Testing

Kinetic Evaluation

Isomerization reactions were carried out in 5 mL heavy-walled reaction vials with a conical bottom (Ace Glass Incorporated) and equipped with triangular triangular spinvane magnetic stirrer (VWR). These vials were heated in a silicone oil bath using a digital temperature-controlled stirring hot plate (Heidloph). A bulk reaction solution consisting of 4 g d-glucose, 36 g DI water and 1 g d-mannitol (internal standard) was prepared. 0.5 g of this solution and 8 mg catalyst (1:350 metal: glucose molar ratio) were added to the reactor. The sealed reactor was then placed in a pre-heated (100° C.) oil bath for fixed intervals of time. The reaction was quenched by placing the reactor in an ice bath for 20-30 min. Weighing the vial before and after the reaction showed no loss of its contents. The reaction mixture was then diluted with 1.5-2.0 DI water. Accurate weights of DI water added for dilution were noted for each sample. The reaction vial was closed and shaken vigorously before sampling using disposable syringes. The sample was then filtered using 0.22 µm nylon (Ø=13 mm) syringe filter and analyzed using High Performance Liquid Chromatography (HPLC) from Waters (Acquity) equipped with a refractive index (RI) detector. Glucose, fructose, mannose, and mannitol concentrations were monitored using Hi-Plex Pb (Agilent) column and PL Hi-Plex Pb (Agilent) guard column using. DI water was used as the mobile phase at a flowrate of 0.60 ml/min and a column temperature of 65° C.

Mechanism Evaluation Test

A solution of 0.5 g d-glucose (deuterated at C-2) from Cambridge isotope was dissolved in 5 mL DI water. 0.5 g of this solution was then added to a 5 mL heavy-walled reaction vials with a conical bottom (Ace Glass Incorporated) and equipped with triangular triangular spinvane magnetic stirrer (VWR). The vial was heated in a silicone oil bath using a digital temperature-controlled stirring hotplate (Heidolph) at (100° C.) oil bath for 5 h. The reaction was quenched using ice-water. Catalyst was filtered using 0.22 μm nylon (Ø=13 mm) syringe filter and the filtrate was concentrated under reduced pressure. The filtrate was then diluted with $D_2O$ (1 mL) and analyzed using $^1H$ and $^{13}C$ nuclear magnetic resonance (NMR) spectroscopy.

Results and Discussion

Figure 13:
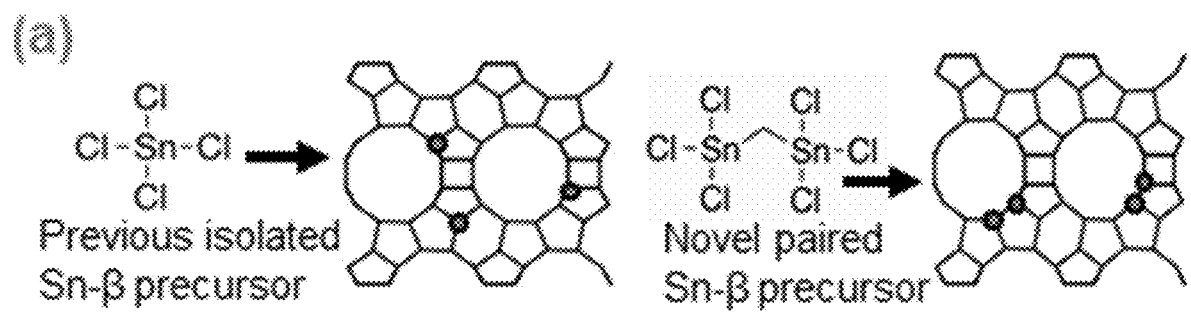
FIG. 13 is a schematic illustration of the synthetic strategy used to introduce paired Lewis acid sites within the crystalline framework of a zeolitic material. For purposes of comparison, previous methods of introducing isolated Lewis acid sites into zeolitic materials are also illustrated.
Figure 14:
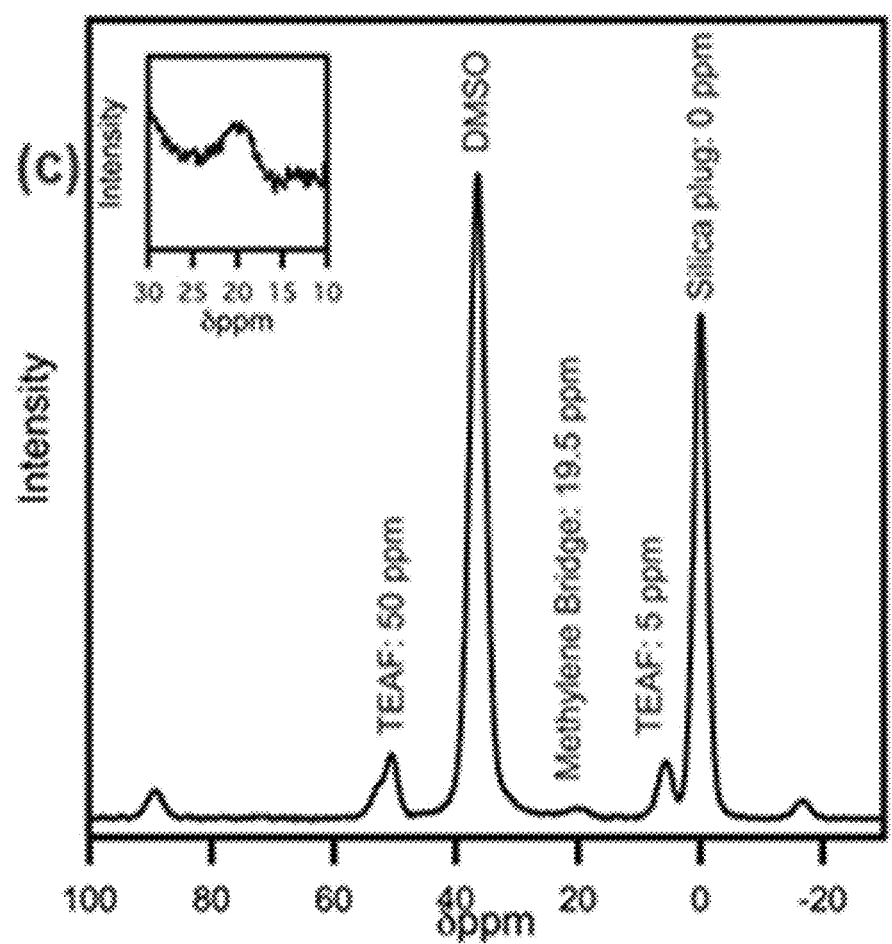
FIG. 14 illustrates the results of NMR studies used to evaluate isolated SnBEA (Si/Sn=100) and paired SnBEA (Si/Sn=100).

The synthesis of zeolitic materials including uniform paired catalytic sites using a paired tin precursor was investigated. Specifically, the synthetic strategy investigated herein utilized a methylene bridged tin dimer (FIG. 13) in fluoride mediated zeolite crystallization conditions.

Figure 15A:
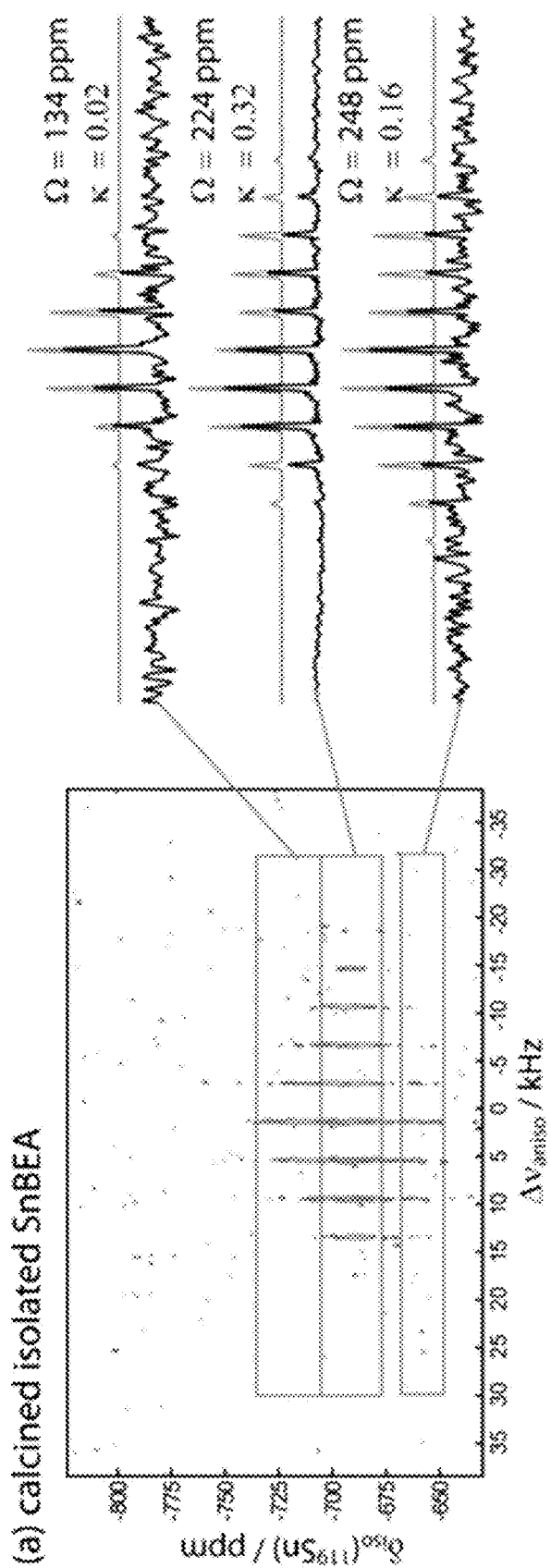
FIG. 15A illustrates the results of NMR studies used to evaluate isolated SnBEA (Si/Sn=100) and paired SnBEA (Si/Sn=100).
Figure 15B:
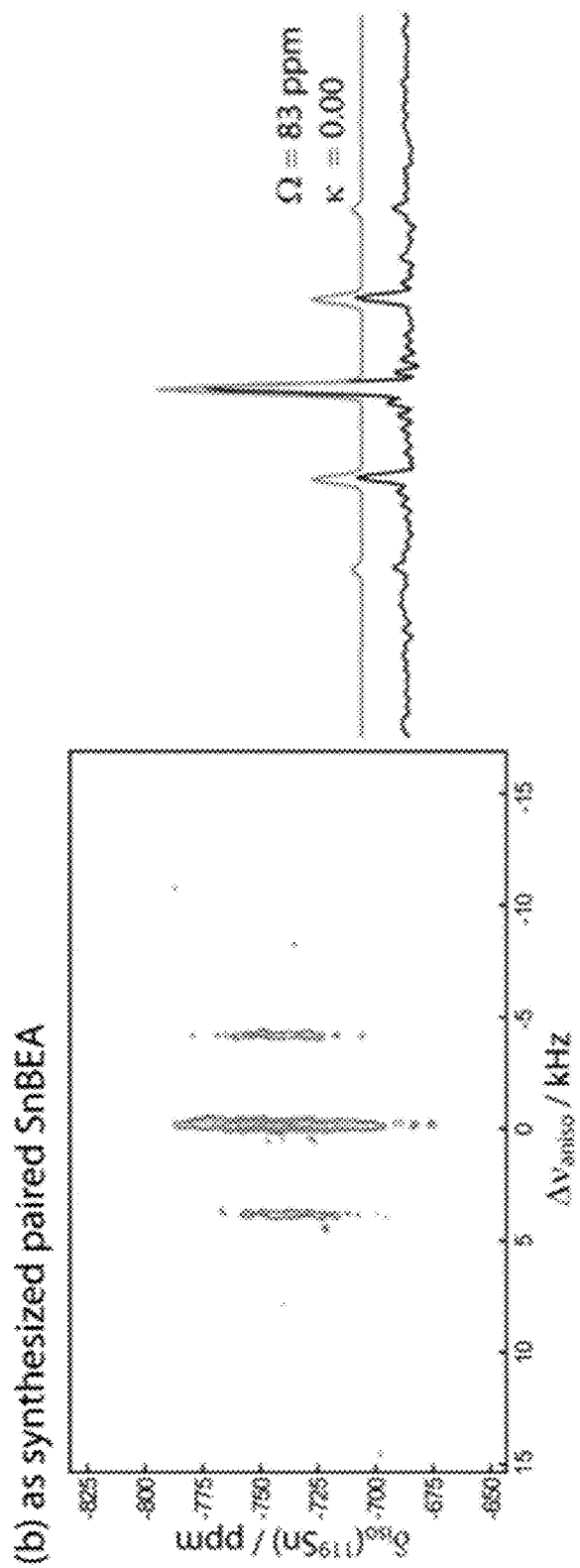
FIG. 15B illustrates the results of NMR studies used to evaluate isolated SnBEA (Si/Sn=100) and paired SnBEA (Si/Sn=100).

The paired tin precursor was synthesized using a multistep synthetic strategy (Schemes 1-2). Similar to the procedure for the isolated site, bis(trichlorostannyl)methane was added to the synthesis gel before adding concentrated HF (final Sn:Si of 1:100). The amount of water was adjusted through rotovapping the mixture before sealing the synthesis gel in a Parr reactor in an oven (temperature 140° C.) equipped with rotating mechanism for 60 days. This crystallization time was longer than the 30 to 40 days required to achieve isolated Sn-BEA, but was used to provide a highly crystalline product. Shorter crystallization times produced amorphous materials when including the paired tin precursor. After crystallization, a highly crystalline zeolite beta material was obtained, as determined from XRD (FIG. 4A, FIG. 15A, and FIG. 15B) and nitrogen physisorption (FIG. 5). XRD spectra were consistent with the IZA database for the BEA framework. Nitrogen physisorption supported the notion that these materials were highly crystalline since the textural properties were similar to materials with isolated Sn sites, consistent with highly crystalline isolated Sn-BEA samples (Table 1). This synthesis method was successfully extended to additional materials such as the MFI framework (XRD in FIG. 4B), demonstrating the inherent flexibility of this approach as suggesting that this approach can be generally applied to prepare other zeolitic materials with paired Lewis acid catalytic sites.

The synthesis produced molecular species and did not form tin oxide clusters, which was demonstrated using DR-UV-vis spectroscopy. DR-UV-vis spectroscopy has been used to probe whether the material contained unwanted clusters of tin oxide (adsorption at 280 nm) or the desirable uniformly dispersed species (adsorption at 240 nm). The DR-UV-vis spectrum for paired Sn-BEA has a sharp adsorption cutoff around 240 nm with no observable peak in the 280 nm range (FIGS. 7A and 7B). This is similar to materials with isolated tin atoms, suggesting that no aggregation occurred to form tin oxide type species. The tin species was confirmed to be incorporated into the material through elemental analysis. The concentration of Si:Sn for paired Sn-BEA is 186:1 while for isolated Sn-BEA a ratio of 118:1 when using a theoretical Si:Sn ratio of 100:1 (Table 2). The lower incorporation of the paired Sn precursor was partially attributed to the transfer process of the chloro-exchanged precursor. For purposes of comparison, isolated Sn-BEA was also synthesized with a Si:Sn of 200:1 to demonstrate that increased in catalytic activity and selectivity was not associated with a concentration dependence.

The successful synthesis of paired Sn-BEA required that the tin dimer remained intact during the crystallization. This was demonstrated using X-ray Absorption Spectroscopy (XAS) (FIGS. 11 and 12) and advanced nuclear magnetic resonance (NMR) methods (FIG. 16A-FIG. 16D) It was determined that that NMR is more suitable for confirming the presence of the paired site. To prevent combustion of the methylene bridge during calcination, the extracted version of paired Sn-BEA was used for the NMR measurements. The characterization of Sn sites in Sn-BEA was particularly challenging due to the $^{119}Sn$'s low natural abundance (8.59%), and the low Sn loadings. However, dynamic nuclear polarization (DNP), which uses unpaired electron spins to hyperpolarize nuclei, can be used to sensitize the detection of $^{119}Sn$ solid-state (SSNMR) in these materials. DNP-enhanced $^{119}Sn$ magic-angle-turning (MAT) experiments can then be performed in order to quantify the chemical shift anisotropy (CSA) of the $^{119}Sn$ sites. Both open and closed $^{119}Sn$ sites in Sn-BEA exhibit large CSA of over 200 ppm caused by the strain that is imposed on Sn because of the shorter Si—O bonds in the network. It was expected that the methylene bridge would enable a greater degree of conformational freedom at the Sn site and allow the formation of a more ideal coordination polyhedron. This would lead to a stark reduction of CSA in paired Sn sites, as confirmed by density functional theory (DFT) calculations.

DNP-enhanced $^{119}Sn$ MAS and MAT SSNMR experiments were performed on Sn-BEA samples possessing either isolated or paired Sn sites. In agreement with previous measurements, a large CSA was observed for both the open ($\Omega$=248 ppm) and closed ($\Omega$=224 ppm) isolated six-coordinate Sn sites, as well as a lower CSA for a surface site ($\Omega$=134 ppm) in agreement with the chemical shift and CSA data measured on SBA-supported Sn sites. In contrast to these results, however, six-coordinate Sn sites possessing a much lower CSA were observed in the paired Sn-BEA materials ($\Omega$=83-100 ppm) thus demonstrating the higher local symmetry at these sites, which is enabled by the more flexible Sn—Sn bridge.

Figure 16A:
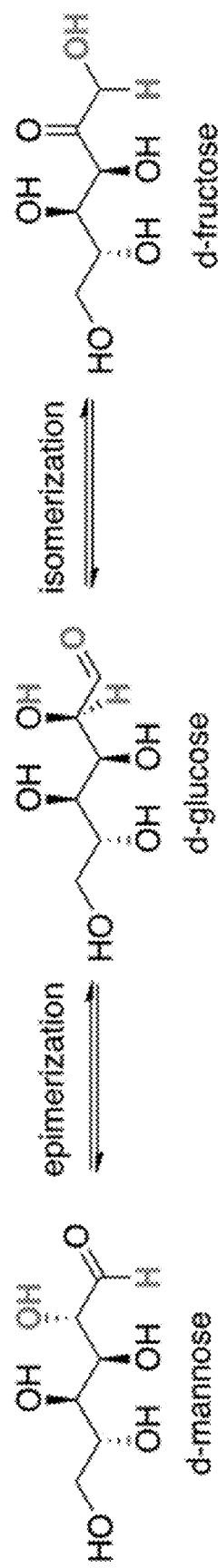
FIG. 16A is a schematic illustration of the Lewis acid catalyzed glucose isomerization to fructose and epimerization to mannose.
Figure 16B:
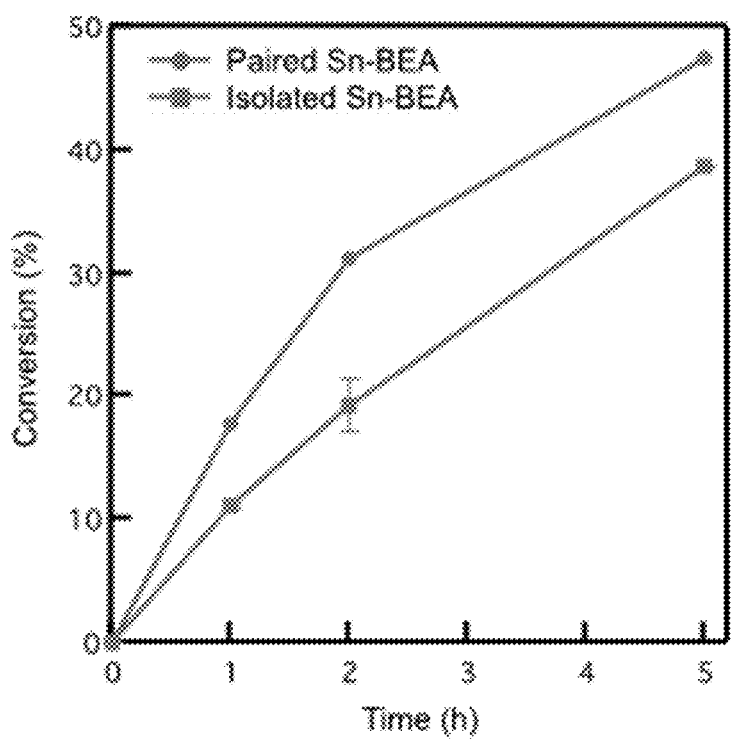
FIG. 16B illustrates the percent conversion to glucose as a function of time for isolated (IC 100) and paired (PC100) Sn-BEA catalysts.
Figure 16C:
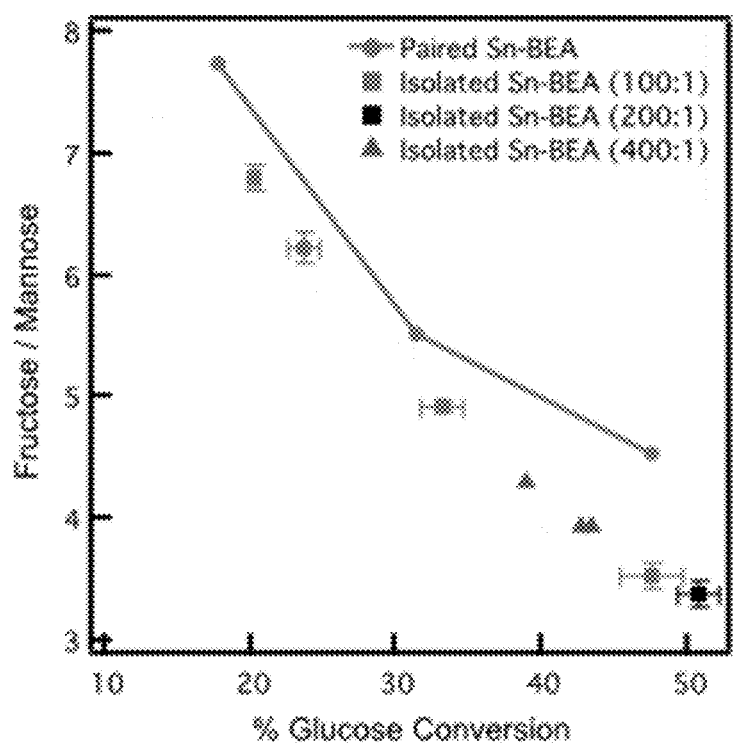
FIG. 16C illustrates the fructose/mannose ratio as a function of percent glucose conversion for isolated (IC 100, IC 200, and IC 400) and paired (PC100) Sn-BEA catalysts.
Figure 16D:
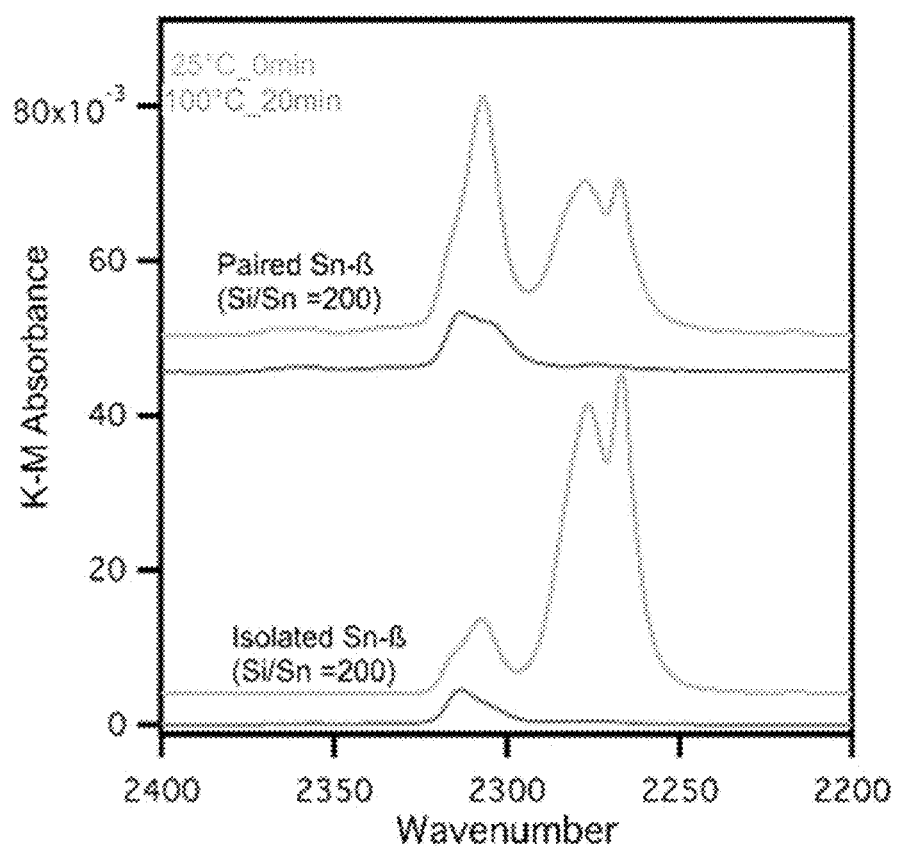
FIG. 16D is a plot of the diffuse-reflectance Fourier transform infrared spectroscopy (DRIFTS) adsorption experiments using deuterated acetonitrile as a probe molecule. Comparison between isolated and paired (Si/Sn=200) shows (i) preferred adsorption on Sn sites of paired Sn-BEA at 25° C. over silanol, in contrast to isolated Sn-BEA, (ii) after heating at 100° C. for 20 min, the residual peak for acetonitrile adsorbed on Sn in paired Sn-BEA is more intense as compared to Sn in isolated Sn-BEA.

The benefit of creating the paired Lewis acid sites with directly adjacent sites in zeolite beta was illustrated by comparing the catalytic activity and selectivity of paired Sn-BEA and isolated Sn-BEA for the isomerization of sugars. Isomerization is known to be equilibrium limited to conversions around 50% with a competing side reaction of epimerization (FIG. 16A). The conversion of glucose for paired and isolated Sn-BEA was compared (FIG. 16B). Using the same tin content, paired Sn-BEA achieved 31% conversion in 2 hours (turnover frequency (TOF) of 0.70 $min^{-1}$) while isolated Sn-BEA only afforded 19% conversion (TOF of 0.39 $min^{-1}$). The calculated TOF for paired Sn-BEA was most likely a lower bound for the actual value since the active site for paired Sn-BEA would include two tin atoms, resulting in a TOF of 1.4 $min^{-1}$. Interestingly, paired Sn-BEA also achieved a greater selectivity for fructose (isomerization):mannose (epimerization) (4.5:1 at 50% conversion) than isolated tin (the range of 3.2-3.5:1 at 50% conversion. See FIG. 16C). For similar conversions, paired Sn-BEA achieved a higher fructose:mannose selectivity than any isolated Sn-BEA catalyst tested. Additionally, the increased selectivity appears to be a general phenomenon since the paired Sn-BEA achieved a higher selectivity than isolated Sn-BEA when converting xylose to xylulose (isomerization product)—paired Sn-BEA achieved a selectivity of 6.5:1 for xylulose:rabinose (epimerization product) compared to 6:1 for isolated Sn-BEA.

The origin of increased catalytic selectivity and activity for paired Sn-BEA could be caused by differences in the nature of the catalytic site available for reaction. In other systems, catalyst selectivity for isomerization has been attributed to the ratio of the "open" vs. "closed" sites. Closed sites are thought to catalyze the epimerization reaction and consist of tin coordinated to four O—Si species; open sites are believed to catalyze the isomerization reaction and consist of tin coordinated to three O—Si species and a stannol adjacent to a silanol. Methods to control the relative amounts of closed and open sites are unknown, the ratios of open to closed sites can be determined through adsorbing deuterated acetonitrile ($CD_3CN$) on the material and measuring the FTIR signal associated with open (2316 $cm^{-1}$) and closed sites (2308 $cm^{-1}$). After degassing the sample at 500° C. and cooling to room temperature under nitrogen flow, both paired and isolated Sn-BEA samples were separately dosed with deuterated acetonitrile and analyzed with FTIR. The FTIR spectra for both isolated and paired Sn-BEA exhibited peaks at similar frequencies for both types of sites that can be assigned to the "open" and "closed" site. Comparing the ratios of the two types of sites for both materials, the measurements of isolated Sn-BEA indicated a greater ratio than paired Sn-BEA of "open" sites to "closed" sites.

The FTIR and catalytic testing results suggest that improved selectivity for the paired site material does not originate from increased number of open sites. Therefore, the increase in selectivity may result from the presence of paired Lewis acid sites in the catalyst. For xylose isomerase enzyme that has a paired catalytic site, the second metal center serves to destabilize sugars that have six-member rings (mannose and glucose) in favor of forming sugars with five-member rings (fructose). A similar mechanism could be responsible for the increased selectivity for the isomerization reaction for paired Sn-BEA. Overall, these results provide indication that molecular tuning of catalytic sites in zeolites through creating Lewis acid pairs can be used to influence catalytic activity and selectivity.

The compositions and methods of the appended claims are not limited in scope by the specific compositions and methods described herein, which are intended as illustrations of a few aspects of the claims. Any compositions and methods that are functionally equivalent are intended to fall within the scope of the claims. Various modifications of the compositions and methods in addition to those shown and described herein are intended to fall within the scope of the appended claims. Further, while only certain representative components and method steps disclosed herein are specifically described, other combinations of the components and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A zeolitic material comprising a microporous crystalline framework substituted with one or more paired Lewis acid sites,
   wherein each of the one or more paired Lewis acid sites comprises a first Lewis acid metal center and a second Lewis acid metal center, and
   wherein the first Lewis acid metal center and the second Lewis acid metal center are separated by three or fewer atoms within the crystalline framework.

2. The zeolitic material of claim 1, wherein each of the one or more paired Lewis acid sites is defined by the formula below

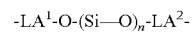

-$LA^1$-O-(Si—O)$_n$-$LA^2$- wherein
   $LA^1$ represents the first Lewis acid metal center;
   $LA^2$ represents the second Lewis acid metal center; and
   n is 0 or 1.

3. The zeolitic material of claim 1, wherein the first Lewis acid metal center and the second Lewis acid metal center are separated by one atom within the crystalline framework.

4. The zeolitic material of claim 1, wherein the first Lewis acid metal center and the second Lewis acid metal center are separated by less than 5 Angstroms.

5. The zeolitic material of claim 1, wherein the first Lewis acid metal center and the second Lewis acid metal center are not Al.

6. The zeolitic material of claim 1, wherein the first Lewis acid metal center and the second Lewis acid metal center are independently chosen from Sn, Hf, Zn, Zr, Ti, V, Ta, Ga, Ge, Nb, and Cr.

7. The zeolitic material of claim 1, wherein the first Lewis acid metal center and the second Lewis acid metal center comprise the same metal.

8. The zeolitic material of claim 1, wherein the first Lewis acid metal center is Sn and the second Lewis acid metal center is Sn.

9. The zeolitic material of claim 1, wherein the first Lewis acid metal center and the second Lewis acid metal center comprise different metals.

10. The zeolitic material of claim 1, wherein the molar ratio of paired Lewis acid sites to Si atoms in the zeolitic material is at least 1:1000.

11. The zeolitic material of claim 1, wherein the molar ratio of paired Lewis acid sites to Si atoms in the zeolitic material is from 1:400 to 1:50.

12. The zeolitic material of claim 1, wherein the microporous crystalline framework comprises BEA or MFI.

13. A method for preparing a zeolitic material comprising a microporous crystalline framework isomorphously substituted with one or more paired Lewis acid sites, the method comprising
   (i) combining, in aqueous solution, a silicon source, a paired Lewis acid monomer, and optionally a structure-directing agent to form a precursor gel;
   (ii) reacting the precursor gel under conditions effective to form a zeolitic precursor; and
   (iii) treating the zeolitic precursor to form the zeolitic material comprising the microporous crystalline framework isomorphously substituted with one or more paired Lewis acid sites.

14. The method of claim 13, wherein step (i) comprises combining, in aqueous solution, the silicon source, the paired Lewis acid monomer, and the structure-directing agent to form a precursor gel.

15. The method of claim 13, wherein step (ii) comprises incubating the precursor gel to hydrolyze the silicon source.

16. The method of claim 13, wherein step (ii) comprises heating the precursor gel in the presence of zeolite seed crystals, a fluoride source, or a combination thereof to form the zeolitic precursor.

17. The method of claim 13, wherein the paired Lewis acid monomer is defined by the formula below

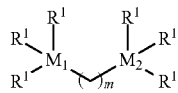

wherein
$M_1$ and $M_2$ are independently chosen from Sn, Hf, Zn, Zr, Ti, V, Ta, Ga, Ge, Nb, and Cr;
$R^1$ represents, independently for each occurrence, a halogen; and
m is an integer from 1 to 5.

18. The method of claim 13, wherein step (iii) comprises calcining the zeolitic precursor to form the zeolitic material comprising the microporous crystalline framework isomorphously substituted with one or more paired Lewis acid sites.

19. The method of claim 18, wherein step (iii) comprises heating the zeolitic precursor in air at a temperature of from 400° C. to 750° C.

20. The method of claim 13, wherein step (iii) comprises extracting the zeolitic precursor to form the zeolitic material comprising the microporous crystalline framework isomorphously substituted with one or more paired Lewis acid sites.

* * * * *